United States Patent
Adams et al.

(10) Patent No.: US 9,676,728 B2
(45) Date of Patent: Jun. 13, 2017

(54) 2-BENZYL-BENZIMIDAZOLE COMPLEMENT FACTOR B INHIBITORS AND USES THEREOF

(71) Applicants: Christopher Adams, Arlington, MA (US); Takeru Ehara, Arlington, MA (US); Keith Jendza, Boston, MA (US); Nan Ji, Arlington, MA (US); Rajeshri Ganesh Karki, Somerville, MA (US); Toshio Kawanami, Belmont, MA (US); Nello Mainolfi, Belmont, MA (US); James Powers, Waltham, MA (US); Michael Serrano-Wu, Belmont, MA (US); Chun Zhang, Waltham, MA (US)

(72) Inventors: Christopher Adams, Arlington, MA (US); Takeru Ehara, Arlington, MA (US); Keith Jendza, Boston, MA (US); Nan Ji, Arlington, MA (US); Rajeshri Ganesh Karki, Somerville, MA (US); Toshio Kawanami, Belmont, MA (US); Nello Mainolfi, Belmont, MA (US); James Powers, Waltham, MA (US); Michael Serrano-Wu, Belmont, MA (US); Chun Zhang, Waltham, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/032,872

(22) PCT Filed: Oct. 29, 2014

(86) PCT No.: PCT/US2014/063009
§ 371 (c)(1),
(2) Date: Apr. 28, 2016

(87) PCT Pub. No.: WO2015/066241
PCT Pub. Date: May 7, 2015

(65) Prior Publication Data
US 2016/0311779 A1    Oct. 27, 2016

Related U.S. Application Data

(60) Provisional application No. 61/897,581, filed on Oct. 30, 2013.

(51) Int. Cl.
| | |
|---|---|
| *C07D 235/10* | (2006.01) |
| *C07D 235/12* | (2006.01) |
| *C07D 235/14* | (2006.01) |
| *C07D 235/16* | (2006.01) |
| *A61K 31/4184* | (2006.01) |
| *A61K 45/06* | (2006.01) |

(52) U.S. Cl.
CPC ........ *C07D 235/12* (2013.01); *A61K 31/4184* (2013.01); *A61K 45/06* (2013.01); *C07D 235/14* (2013.01)

(58) Field of Classification Search
CPC .. C07D 235/10; C07D 235/12; C07D 235/14; C07D 235/16
See application file for complete search history.

(56) References Cited

U.S. PATENT DOCUMENTS

| | | | |
|---|---|---|---|
| 4,859,684 | A | 8/1989 | Raeymaekers et al. |
| 5,342,957 | A | 8/1994 | Van Wauwe et al. |
| 5,409,929 | A | 4/1995 | Ciganek |
| 5,763,688 | A | 6/1998 | Ikariya et al. |
| 8,012,682 | B2 | 9/2011 | Lukyanov et al. |
| 9,056,874 | B2 | 6/2015 | Adams et al. |
| 2007/0259936 | A1 | 11/2007 | Player et al. |
| 2008/0146501 | A1 | 6/2008 | Hageman et al. |
| 2008/0255000 | A1 | 10/2008 | Dogulu et al. |
| 2008/0280825 | A1 | 11/2008 | Hageman et al. |
| 2009/0111708 | A1 | 4/2009 | Seddon et al. |
| 2009/0214538 | A1 | 8/2009 | Fung et al. |
| 2009/0221665 | A1 | 9/2009 | Earnest |
| 2010/0069468 | A1 | 3/2010 | Hess et al. |
| 2010/0120665 | A1 | 5/2010 | Kaleko et al. |

(Continued)

FOREIGN PATENT DOCUMENTS

| | | |
|---|---|---|
| CN | 1285557 | 11/2006 |
| EP | 0426225 A2 | 5/1991 |

(Continued)

OTHER PUBLICATIONS

Barnes et al., European Respiratory Journal (2005), 25(6), pp. 1084-1106.

(Continued)

*Primary Examiner* — Laura L. Stockton
(74) *Attorney, Agent, or Firm* — Shawn D. Britt

(57) ABSTRACT

The present invention provides a compound of formula (I) a method for manufacturing the compounds of the invention, and its therapeutic uses. The present invention further provides a combination of pharmacologically active agents and a pharmaceutical composition.

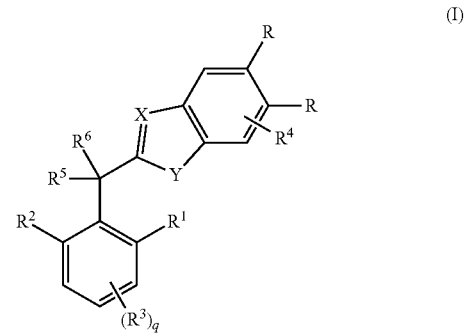

12 Claims, No Drawings

(56) References Cited

U.S. PATENT DOCUMENTS

| | | |
|---|---|---|
| 2010/0166862 A1 | 7/2010 | Francois et al. |
| 2010/0273720 A1 | 10/2010 | Hageman et al. |
| 2011/0114888 A1 | 5/2011 | Akino |
| 2011/0117557 A1 | 5/2011 | Canter et al. |
| 2011/0229439 A1 | 9/2011 | Humphnes et al. |
| 2012/0071356 A1 | 3/2012 | Allikmets et al. |
| 2015/0250767 A1 | 9/2015 | Adams et al. |
| 2016/0024079 A1 | 1/2016 | Adams et al. |

FOREIGN PATENT DOCUMENTS

| | | |
|---|---|---|
| EP | 2 578 573 A1 | 4/2013 |
| JP | 2010037511 | 4/2010 |
| WO | 9504052 A1 | 2/1995 |
| WO | 9707097 A1 | 2/1997 |
| WO | 99/40072 A1 | 8/1999 |
| WO | 2004/069256 | 8/2004 |
| WO | 2005/002520 A2 | 1/2005 |
| WO | 2005/037829 A1 | 4/2005 |
| WO | 2006/041872 A2 | 4/2006 |
| WO | 2006/084338 A1 | 8/2006 |
| WO | 2006/099379 A2 | 9/2006 |
| WO | 2006/125324 A1 | 11/2006 |
| WO | 2007/056111 | 5/2007 |
| WO | 2007/095185 | 8/2007 |
| WO | 2007/095287 | 8/2007 |
| WO | 2008/003703 A1 | 1/2008 |
| WO | 2008/106644 | 9/2008 |
| WO | 2008/140793 | 11/2008 |
| WO | 2009/073564 A1 | 6/2009 |
| WO | 2009/105757 | 8/2009 |
| WO | 2009/157429 A1 | 12/2009 |
| WO | 2010/029162 | 3/2010 |
| WO | 2010/066684 A2 | 6/2010 |
| WO | 2010/085542 | 7/2010 |
| WO | 2010/127152 A2 | 11/2010 |
| WO | 2011/017229 | 2/2011 |
| WO | 2013/016197 A1 | 1/2013 |
| WO | 2013/164802 A1 | 11/2013 |

OTHER PUBLICATIONS

Doan et al., The Journal of Clinical Pharmacology, (2005), 45, pp. 751-762.

Li Qian et al., Journal of Neural Transmission, (2010), 117(8), pp. 971-979.

Guttman et al., Canadian Medical Association Journal, (2003), 168(3), pp. 293-301.

Knaryan et al., Journal of Neurochemistry, (2011), 118, pp. 326-338.

Le et al., The Journal of Biological CHemistry, (2007) 282(48), pp. 34809-34816.

Ruiz-Gomez et al., Journal of MEdical Chemistry, (2009), 52, pp. 6042-6052.

2-BENZYL-BENZIMIDAZOLE COMPLEMENT FACTOR B INHIBITORS AND USES THEREOF

This application is a U.S. National Phase filing of International Application No. PCT/US2014/063009 filed 29 Oct. 2014, which claims priority to U.S. Application No. 61/897,581 filed 30 Oct. 2013.

FIELD OF THE INVENTION

The invention relates to the inhibition of the complement alternative pathway and particularly to inhibition of Factor B, in patients suffering from conditions and diseases associated with complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor B may be a suitable target for the inhibition of this amplification of the complement pathways because its plasma concentration in humans is typically about 200 µg/mL (or about 2 µM), and it has been shown to be a critical enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganglion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from Intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H (CFH) (Edwards A O, et al. Complement factor H polymorphism and age-related macular degeneration. Science. 2005 Apr. 15; 308(5720):421-4; Hageman G S, et al A common haplotype in the complement regulatory gene factor H (HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol Vis Sci. 2006 August; 47(8):3242-6; Simonelli F, et al. Polymorphism p.402Y>H in the complement factor H protein is a risk factor for age related macular degeneration in an Italian population. Br J Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53.), complement factor B (CFB) and complement C2 (Gold B, et al. Variation in factor B (BF) and complement component 2 (C2) genes is associated with age-related macular degeneration. Nat Genet. 2006 April; 38(4):458-62 and Jakobsdottir J, et al. C2 and CFB genes image-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Mailer J B, et al Variation in complement factor 3 is associated with risk of age-related macular degeneration. Nat Genet. 2007 October; 39(10):1200-1 and Park K H, et al Complement component 3 (C3) haplotypes and risk of advanced age-related macular degeneration. Invest Ophthalmol Vis Sci. 2009 July; 50(7):3386-93. Epub 2009 Feb. 21.). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation of the alternative complement pathway. In certain embodiments, the present invention provides compounds that modulate, and preferably inhibit, Factor B activity and/or Factor B mediated complement pathway activation. Such Factor B modulators are preferably high affinity Factor B inhibitors that inhibit the catalytic activity of complement Factor B, such as primate Factor B and particularly human Factor B.

The compounds of the present invention inhibit or suppress the amplification of the complement system caused by C3 activation irrespective of the initial mechanism of activation (including for example activation of the classical, lectin or alternative pathways).

Various embodiments of the invention are described herein. It will be recognized that features specified in each embodiment may be combined with other specified features to provide further embodiments.

Within certain aspects, Factor B modulators provided herein are compounds of Formula I and salts and tautomers thereof:

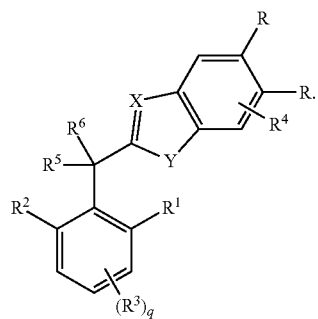

(I)

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more additional therapeutically active agents.

The invention further provides methods of treating or preventing complement mediated diseases, the method comprising the steps of identifying a patient in need of complement modulation therapy and administering a compound of Formula (I) or a subformulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

DETAILED DESCRIPTION OF THE INVENTION

As noted above, the present invention provides compounds that modulate Factor B activation and/or Factor B-mediated signal transduction of the complement system. Such compounds may be used in vitro or in vivo to modulate (preferably inhibit) Factor B activity in a variety of contexts.

The invention related generally to compounds of Formula I and salts and tautomers thereof which modulation the alternative pathway of the complement system. Compounds of Formula I are generally represented by the structure:

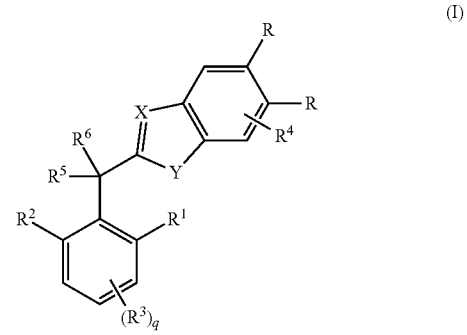

(I)

Wherein
X is N or CH;
Y is N(H), O or S;
one occurrence of R is cyano and the other occurrence of R is hydrogen or $R^4$;
$R^1$ is hydrogen, halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, halo$C_1$-$C_6$alkoxy, or $S(O)_pC_1$-$C_6$alkyl;
$R^2$ is halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, or $S(O)_pC_1$-$C_6$alkyl;
p is 0, 1, or 2;
q is 0, 1, or 2;
$R^3$ is hydrogen, halogen, cyano, $C_1$-$C_4$alkyl, halo$C_1$-$C_4$alkyl $C_1$-$C_4$alkoxy, or halo$C_1$-$C_4$alkoxy;
$R^4$ is 0, 1, or 2 substitutents independently selected at each occurrence from halogen and $C_1$-$C_6$alkyl;
$R^5$ is hydrogen, $C_1$-$C_6$alkyl, halo$C_1$-$C_6$alkyl, or $C_3$-$C_6$cycloalkyl;
$R^6$ is hydroxy, amino, $C_1$-$C_6$alkyl, $C_1$-$C_6$alkoxy, $C_1$-$C_4$haloalkoxy, $C_1$-$C_6$alkoxy$C_1$-$C_6$alkoxy, mono- and di-$C_1$-$C_4$alkylamino, amino $C_1$-$C_6$alkylamino, $[CR^8{}_2]_nR^7$, $[CR^8{}_2]_nC(O)R^7$, $O[CR^8{}_2]_nR^7$, NHC(O)$C_1$-$C_6$alkyl, NHS$(O_2)C_1$-$C_6$alkyl, $(CH_2)_nR^9$, $O(CH_2)_nR^9$, $C(O)R^7$, N(H)$[CR^A{}_2]_nR^7$, $O[CR^A{}_2]_nC(O)R^7$, N(H)$[CR^8{}_2]_nC(O)R^7$ or tetrazolyl;
n is 1, 2, 3 or 4;

$R^7$ is hydroxy, $C_1$-$C_4$alkoxy, amino or mono- and di-$C_1$-$C_4$alkylamino;
$R^8$ is independently selected at each occurrence from hydrogen, halogen or $C_1$-$C_4$alkyl;
$R^9$ is a 5 member heteroaryl having 1 to 4 ring heteroatoms selected from N, O or S and optionally substituted with 0, 1, or 2 $C_1$-$C_4$alkyl groups, with the proviso that when Y is S, $R^6$ is hydroxy and $R^2$ is halogen, then $R^5$ is not halo$C_1$-$C_6$alkyl.

In a first embodiment, the invention provides compounds of Formula I and salts and tautomers thereof, which modulate the alternative pathway of the complement system. Compounds of Formula I are represented by the structure:

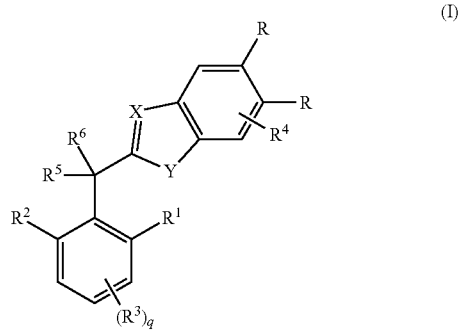

(I)

Wherein
X is N or CH;
Y is N(H) or O;
one occurrence of R is cyano and the other occurrence of R is hydrogen or $R^4$;
$R^1$ is hydrogen, halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, halo$C_1$-$C_6$alkoxy, or $S(O)_pC_1$-$C_6$alkyl;
$R^2$ is halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, or $S(O)_pC_1$-$C_6$alkyl;
p is 0, 1, or 2;
q is 0, 1, or 2;
$R^3$ is hydrogen, halogen, cyano, $C_1$-$C_4$alkyl, halo$C_1$-$C_4$alkyl $C_1$-$C_4$alkoxy, or halo$C_1$-$C_4$alkoxy;
$R^4$ is 0, 1, or 2 substituents independently selected at each occurrence from halogen and $C_1$-$C_6$alkyl;
$R^5$ is hydrogen, $C_1$-$C_6$alkyl, halo$C_1$-$C_6$alkyl, or $C_3$-$C_6$cycloalkyl;
$R^6$ is hydroxy, amino, $C_1$-$C_6$alkyl, $C_1$-$C_6$alkoxy, $C_1$-$C_4$haloalkoxy, $C_1$-$C_6$alkoxy$C_1$-$C_6$alkoxy, mono- and di-$C_1$-$C_4$alkylamino, amino $C_1$-$C_6$alkylamino, $[CR^8{}_2]_nR^7$, $[CR^8{}_2]_nC(O)R^7$, $O[CR^8{}_2]_nR^7$, $NHC(O)C_1$-$C_6$alkyl, $NHS(O_2)C_1$-$C_6$alkyl, $(CH_2)_nR^9$, $O(CH_2)_nR^9$, $C(O)R^7$, $N(H)[CR^4{}_2]_nR^7$, $O[CR^4{}_2]_nC(O)R^7$, $N(H)[CR^8{}_2]_nC(O)R^7$ or tetrazolyl;
n is 1, 2, 3 or 4;
$R^7$ is hydroxy, $C_1$-$C_4$alkoxy, amino or mono- and di-$C_1$-$C_4$alkylamino;
$R^8$ is independently selected at each occurrence from hydrogen, halogen or $C_1$-$C_4$alkyl;
$R^9$ is a 5 member heteroaryl having 1 to 4 ring heteroatoms selected from N, O or S and optionally substituted with 0, 1, or 2 $C_1$-$C_4$alkyl groups.

In a second embodiment, the invention provides compounds of embodiment one in which X is N and Y is N(H) or O. In a third embodiment, the invention provides compounds of embodiment one in which X is N and Y is N(H). In a fourth embodiment, the invention provides compounds of any one of embodiments one to three in which $R^4$ is absent.

In a fifth embodiment, the invention provides compounds of any one of embodiments one to four in which $R^1$ is hydrogen, $C_1$-$C_4$alkyl or $C_1$-$C_4$alkoxy.

In a sixth embodiment, the invention provides compounds of any one of embodiments one to five in which $R^2$ is $C_1$-$C_4$alkyl or $C_1$-$C_4$alkoxy.

In a seventh embodiment, the invention provides compounds of any one of embodiments one to six or salt or tautomer thereof in which the compounds are represented by Formula (II):

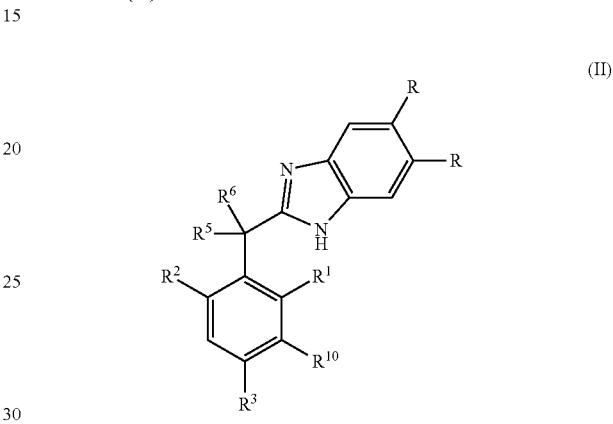

(II)

Wherein one occurrence of R is cyano and the other occurrence of R is hydrogen;
$R^1$ is hydrogen, methyl, methoxy, ethyl or ethyoxy;
$R^2$ is methyl, methoxy, ethyl or ethyoxy;
$R^3$ is hydrogen, methyl, methoxy, ethyl or ethyoxy; and
$R^{10}$ is hydrogen or halogen.

In an eighth embodiment, the invention provides compounds of any one of embodiments one to seven in which $R^5$ is hydrogen, $C_1$-$C_4$alkyl, halo $C_1$-$C_4$alkyl, or $C_3$-$C_6$cycloalkyl.

In a ninth embodiment, the invention provides compounds of any one of embodiments one to eight in which $R^6$ is hydroxyl, amino, $C_1$-$C_4$alkyl, methoxy, trifluoromethoxy, mono- and di-$C_1$-$C_4$alkyl amino, or $CH_2C(O)NH_2$.

In a tenth embodiment, the invention provides compounds of any one of embodiments one to nine in which X is N; Y is N(H);
One occurrence of R is cyano and the other occurrence of R is hydrogen;
$R^1$ is hydrogen, methyl, methoxy, ethyl or ethyoxy;
$R^2$ is methyl, methoxy, ethyl or ethyoxy;
$R^3$ is hydrogen or methyl;
$R^4$ is absent;
$R^5$ is hydroxyl, amino, methoxy, trifluoromethoxy, methylamino or $CH_2C(O)NH_2$;
$R^6$ is hydrogen, methyl, cyclopropyl or trifluoromethyl; and
$R^{10}$ is hydrogen, chloro or bromo.

In an eleventh embodiment, the invention provides compounds of embodiment one or a salt, stereoisomer or tautomer thereof in which the compound is selected from the group consisting of
(±)-2-(Hydroxy(2-methoxy-4,6-dimethylphenyl)methyl)-1H-benzo[d]imidazole-5-carbonitrile;
(±)-2-(1-Hydroxy-1-(2-methoxy-4,6-dimethylphenyl) ethyl)-1H-benzo[d]imidazole-5-carbonitrile;
(±)-2-(2,2,2-Trifluoro-1-hydroxy-1-(2-methoxy-4,6-dimethylphenyl)ethyl)-1H-benzo[d]imidazole-5-carbonitrile;

(±)-2-(1-(3-bromo-6-methoxy-2,4-dimethylphenyl)-2,2,2-trifluoro-1-hydroxyethyl)-1H-benzo[d]imidazole-5-carbonitrile;

(+) or (−)-2-(2,2,2-Trifluoro-1-(2-methoxy-4,6-dimethylphenyl)-1-(methylamino)ethyl)-1H-benzo[d]imidazole-5-carbonitrile;

(−) or (+)-2-(2,2,2-Trifluoro-1-(2-methoxy-4,6-dimethylphenyl)-1-(methylamino)ethyl)-1H-benzo[d]imidazole-5-carbonitrile;

(±)-2-(2,2,2-Trifluoro-1-(2-methoxy-4-methylphenyl)-1-(methylamino)ethyl)-1H-benzo[d]imidazole-5-carbonitrile;

(±)-2-(1-(3-Chloro-6-methoxy-2,4-dimethylphenyl)-2,2,2-trifluoro-1-(methylamino)ethyl)-1H-benzo[d]imidazole-5-carbonitrile;

(±)-2-(2,2,2-Trifluoro-1-(2-methoxy-6-methylphenyl)-1-(methylamino)ethyl)-1H-benzo[d]imidazole-5-carbonitrile;

(±)-2-(1-Amino-2,2,2-trifluoro-1-(2-methoxy-4,6-dimethylphenyl)ethyl)-1H-benzo[d]imidazole-5-carbonitrile;

(±)-2-(1-(3-Bromo-6-methoxy-2,4-dimethylphenyl)-2,2,2-trifluoro-1-(methylamino)ethyl)-1H-benzo[d]imidazole-5-carbonitrile;

(±)-2-(Amino(2-methoxy-4,6-dimethylphenyl)methyl)-1H-benzo[d]imidazole-5-carbonitrile;

(±)-2-(1-Amino-1-(2-methoxy-4,6-dimethylphenyl)ethyl)-1H-benzo[d]imidazole-5-carbonitrile;

(±)-2-(Amino(cyclopropyl)(2-methoxy-4,6-dimethylphenyl)methyl)-1H-benzo[d]imidazole-5-carbonitrile;

(±)-2-(1-(5-Cyano-1H-benzo[d]imidazol-2-yl)-2,2,2-trifluoro-1-(2-methoxy-4,6-dimethylphenyl)ethoxy)acetamide;

(+) or (−)-2-(2,2,2-trifluoro-1-methoxy-1-(2-methoxy-4,6-dimethylphenyl)ethyl)-1H-benzo[d]imidazole-5-carbonitrile;

(−) or (+)-2-(2,2,2-trifluoro-1-methoxy-1-(2-methoxy-4,6-dimethylphenyl)ethyl)-1H-benzo[d]imidazole-5-carbonitrile;

(±)-2-((2,6-Dimethoxy-4-methylphenyl)(methylamino)methyl)-1H-benzo[d]imidazole-5-carbonitrile;

(±)-2-(1-(2,6-dimethoxy-4-methylphenyl)-2,2,2-trifluoro-1-(methylamino)ethyl)-1H-benzo[d]imidazole-5-carbonitrile and salts, stereoisomers and tautomers thereof.

In another embodiment, pharmaceutical compositions are provided which comprise one or more pharmaceutically acceptable carriers and a therapeutically effective amount of a compound of any one of formulae I, II, or a subformulae thereof.

In another embodiment, combinations, in particular pharmaceutical combinations, are provided which comprise a therapeutically effective amount of the compound any one of formulae I, II, or a subformulae thereof.

In another embodiment, methods of modulating complement alternative pathway activity in a subject are provided which methods comprise administering to the subject a therapeutically effective amount of any one of formulae I, II, or a subformulae thereof.

In yet other embodiments, methods of treating a disorder or a disease in a subject mediated by complement activation, in particular mediated by activation of the complement alternative pathway, are provided, which methods comprise administering to the subject a therapeutically effective amount of the compound of any one of formulae I, II or a subformulae thereof.

In another embodiment, methods of treating age related macular degeneration in a subject are provided which methods comprise administering to the subject a therapeutically effective amount of the compound of any one of formulae I, II, or a subformulae thereof.

In another aspect, the invention provides for the use of compounds of any one of formulae I, II, or a subformulae thereof for use in the preparation of a medicament and more particularly for use in the manufacture of a medicament for the treatment of a disorder or disease in a subject mediated by complement activation or activation of the complement alternative pathway. In certain other aspects, the invention provides for the use of a compound according of any one of formulae I, II, or a subformulae thereof in the treatment of age-related macular degeneration.

In one embodiment, the invention provides a combination, in particular a pharmaceutical combination, comprising a therapeutically effective amount of the compound according to the definition of formula I, II or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1, 4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
  (a) alkyl;
  (b) hydroxy (or protected hydroxy);
  (c) halo;
  (d) oxo, i.e., =O;
  (e) amino, alkylamino or dialkylamino;
  (f) alkoxy;
  (g) cycloalkyl;
  (h) carboxyl;
  (i) heterocyclooxy, wherein heterocyclooxy denotes a heterocyclic group bonded through an oxygen bridge;
  (j) alkyl-O—C(O)—;
  (k) mercapto;
  (l) nitro;
  (m) cyano;
  (n) sulfamoyl or sulfonamido;
  (o) aryl;
  (p) alkyl-C(O)—O—;
  (q) aryl-C(O)—O—;
  (r) aryl-S—;
  (s) aryloxy;
  (t) alkyl-S—;
  (u) formyl, i.e., HC(O)—;
  (v) carbamoyl;
  (w) aryl-alkyl-; and
  (x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolylcarbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
 (a) alkyl;
 (b) hydroxy (or protected hydroxy);
 (c) halo;
 (d) oxo, i.e., =O;
 (e) amino, alkylamino or dialkylamino;
 (f) alkoxy;
 (g) cycloalkyl;
 (h) carboxyl;
 (i) heterocyclooxy, wherein heterocyclooxy denotes a heterocyclic group bonded through an oxygen bridge;
 (j) alkyl-O—C(O)—;
 (k) mercapto;
 (l) nitro;
 (m) cyano;
 (n) sulfamoyl or sulfonamido;
 (o) aryl;
 (p) alkyl-C(O)—O—;
 (q) aryl-C(O)—O—;
 (r) aryl-S—;
 (s) aryloxy;
 (t) alkyl-S—;
 (u) formyl, i.e., HC(O)—;
 (v) carbamoyl;
 (w) aryl-alkyl-; and
 (x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
 (a) alkyl;
 (b) hydroxy (or protected hydroxy);
 (c) halo;
 (d) oxo, i.e., =O;
 (e) amino, alkylamino or dialkylamino;
 (f) alkoxy;
 (g) cycloalkyl;
 (h) carboxyl;
 (i) heterocyclooxy, wherein heterocyclooxy denotes a heterocyclic group bonded through an oxygen bridge;
 (j) alkyl-O—C(O)—;
 (k) mercapto;
 (l) nitro;
 (m) cyano;
 (n) sulfamoyl or sulfonamido;
 (o) aryl;
 (p) alkyl-C(O)—O—;
 (q) aryl-C(O)—O—;
 (r) aryl-S—;
 (s) aryloxy;
 (t) alkyl-S—;
 (u) formyl, i.e., HC(O)—;
 (v) carbamoyl;
 (w) aryl-alkyl-; and
 (x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The use of "rel" indicates that the diastereomeric orientation is known but the absolute stereochemistry is not. In cases where the absolute stereochemistry has not been determined the optical rotation and/or chiral chromatography conditions will indicate which isomer is present.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line or retention time on chiral chromatography separation. Certain of the compounds described herein contain one or more asymmetric centers or axes and may thus give rise to enantiomers, diastereomers, and other stereoisomeric forms that may be defined, in terms of absolute stereochemistry, as (R)- or (S)-, or with the (+) or (−) sign. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesuflonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, ch lortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{124}I$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) include deuteration of $R^1$, $R^3$, $R^5$ and/or $R^6$, for example when any of $R^1$, $R^3$, $R^5$ and/or $R^6$ are methyl, methoxy, or ethoxy, the alkyl residue is preferably deuterated, e.g. $CD_3$, $OCD_3$ or $OC_2D_5$. when $R^3$ is alkanoyl, e.g., $C(O)CD_3$.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor B, or (ii) associated with Factor B activity, or (iii) characterized by activity (normal or abnormal) of the complement alternative pathway; or (2) reducing or inhibiting the activity of Factor B; or (3) reducing or inhibiting the expression of Factor B; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor B and/or the complement alternative pathway; or at least partially reducing or inhibiting the expression of Factor B and/or the complement alternative pathway. The meaning of the term "a therapeutically effective amount" as illustrated in the above embodiment for Factor B and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethyl-hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

General Synthetic Aspects

The following Examples serve to illustrate the invention without limiting the scope thereof.

Typically, the compounds of formula (I) can be prepared according to the Schemes provided below.

Compounds such as S-3 (Scheme 1) where X is N or CH; Y is NSEM, O or S; one occurrence of R is cyano and the other occurrence of R is hydrogen or $R^4$ and C is 0, 1, or 2 substitutents independently selected at each occurrence from halogen and $C_1$-$C_6$alkyl and $R^1$ is hydrogen, halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, halo$C_1$-$C_6$alkoxy, or $S(O)_p$ $C_1$-$C_6$alkyl and $R^2$ is halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, or $S(O)_p C_1$-$C_6$alkyl and $R^3$ is hydrogen, halogen, cyano, $C_1$-$C_4$alkyl, halo$C_1$-$C_4$alkyl $C_1$-$C_4$alkoxy, or halo$C_1$-$C_4$alkoxy and q is 0, 1, or 2 and $R^5$=H and $R^6$=OH can be derivatized from the nucleophilic addition of the deprotonated heterocycles such as S-2 (using a base such as LDA at low temperatures such as –78° C.) and aldehydes such as S-1 with the appropriate substitution reflected in S-3. Deprotonation of S-3 with HCl in MeOH would remove the SEM protecting group when Y=NSEM.

Scheme 1.

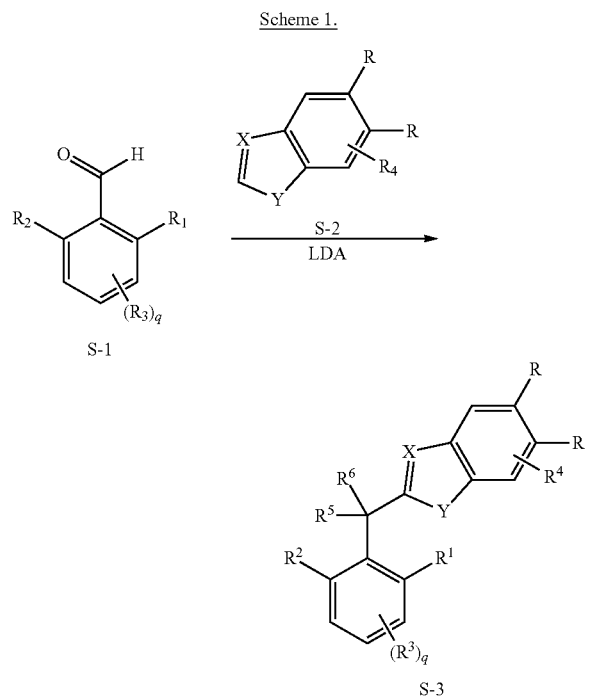

Compound such as S-3 where $R^5$=H and $R^6$=OH can be oxisized with $MnO_2$ in a solvent such as DCM or toluene at temperatures between rt and 60° C. to give compounds such as S-4 (Scheme 2). Addition of alkyl Grignards or trifluoromethyltrimethylsilane in presence of TBAF in THF at temperatures between –78° C. and room temperature can give compounds such as S-5 where $R^5$ is hydrogen, $C_1$-$C_6$alkyl, halo$C_1$-$C_6$alkyl, or $C_3$-$C_6$cycloalkyl; and $R^6$ is either OH or $C_1$-$C_6$alkoxy, $C_1$-$C_4$haloalkoxy, $C_1$-$C_6$alkoxy$C_1$-$C_6$alkoxy, $O[CR^8_2]_nR^7$, $O(CH_2)_nR^9$, $O[CR^A_2]_nC(O)R^7$ where: $R^7$ is hydroxy, $C_1$-$C_4$alkoxy, amino or mono- and di-$C_1$-$C_4$alkylamino; $R^8$ is independently selected at each occurrence from hydrogen, halogen or $C_1$-$C_4$alkyl; $R^9$ is a 5 member heteroaryl having 1 to 4 ring heteroatoms selected from N, O or S and optionally substituted with 0, 1, or 2 $C_1$-$C_4$alkyl groups upon further alkylation of the OH with an appropriate electrophile in the presence of a base such as NaH in solvents such as THF or DMF at 0° C. and or room temperature. Compounds such as S-6 where $R^5$ is halo$C_1$-$C_6$alkyl, and $R^6$ is amino, mono- and di-$C_1$-$C_4$alkylamino, can be accessed by compounds such as S-5 where $R^5$=$CF_3$ and $R^6$=OH. Removal of the SEM group from S-5 (Y=N-SEM) can be accomplished by treatment with HCl in MeOH at 60° C., or by employing TBAF in the presence of ethylenediamine in THF at temperatures between room temperature and 70° C. preferably 60° C. Treatment of the resulting compound with $SOCl_2$ in the presence of a catalytic amount of DMF in $CH_3Cl$ at 60° C. followed by reaction with alcoholic solutions of amines such 2M ammonia in EtOH or 33% methylamine in EtOH afford the wanted compounds S-6. Compounds such as S-8 where $R^5$ is hydrogen, $C_1$-$C_6$alkyl, halo$C_1$-$C_6$alkyl, or $C_3$-$C_6$cycloalkyl; $R^6$ is amino, mono- and di-$C_1$-$C_4$alkylamino, amino $C_1$-$C_6$alkylamino, $[NHC(O)C_1$-$C_6$alkyl, $NHS(O_2)C_1$-$C_6$alkyl, $N(H)[CR^A_2]_nR^7$, $N(H)[CR^8_2]_nC(O)R^7$ can be derived from compounds such as S-4. The ketone wherein can be transformed into the sulfinyl imine S-7 by employing a dehydrating reagent such $Ti(O$-$i$-$Pr_4)$ in the presence of tert-butyl sulfinamide without the need for additional solvent. Alternatively, the dehydration can be achieved by utilizing $Zr(O$-$t$-$Bu)_4$ in a suitable solvent such as toluene. The sulfinyl imine S-7 can be reacted with a suitable organometallic nucleophile such as MeMgI, followed by treatment with HCl in MeOH to furnish S-8. Alternatively, S-7 can be reduced with $NaBH_4$ in MeOH to afford compounds wherein $R^5$ is hydrogen, and the resulted sulfinyl group can then be removed by treatment with HCl in MeOH to afford S-8. The amino group of S-8 can be further alkylayted with an appropriate electrophile in the presence of a base such as NaH in solvents such as THF or DMF at 0° C. and or room temperature or using the appropriate aldehyde in a reductive amination type reaction.

Scheme 2.

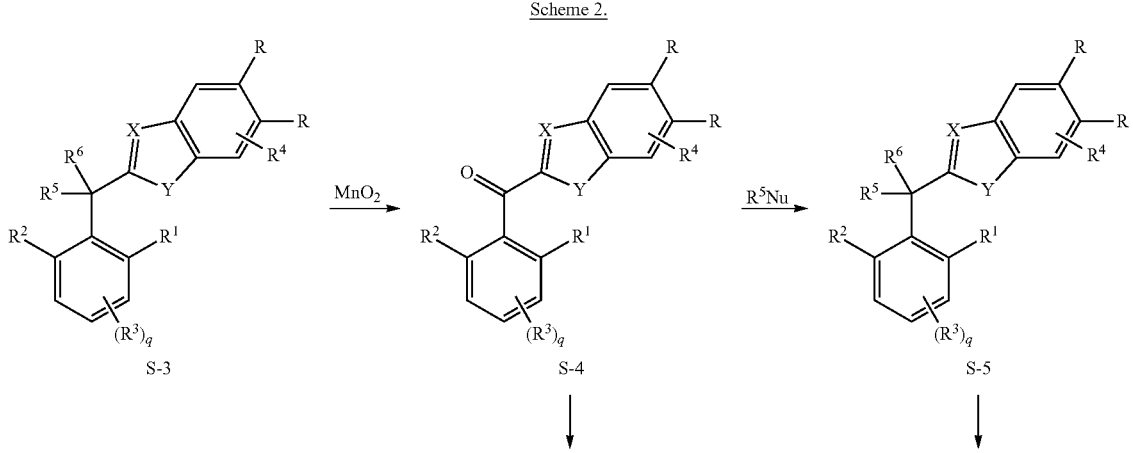

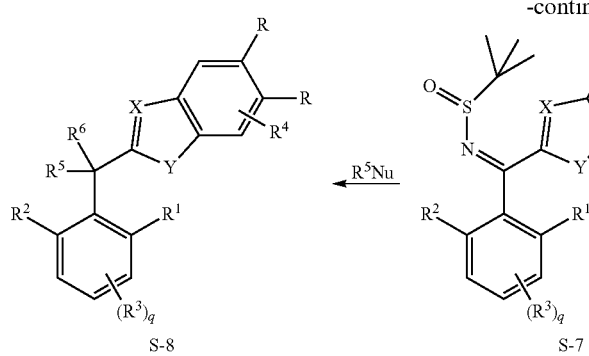
S-8

-continued

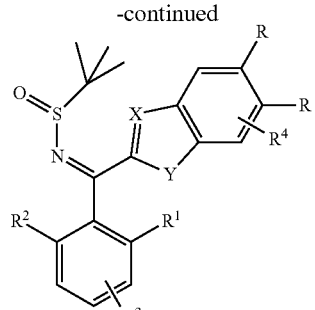
S-7

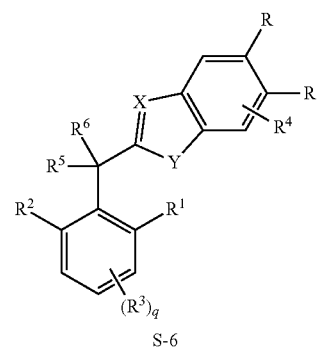
S-6

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art. All tautomeric forms are also intended to be included.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.
Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Ophthalmic formulations, eye ointments, powders, solutions, suspensions and the like, for topical administration are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor B modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing compelment mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, anca vasculitis, cryoglobulinemia, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), dense deposit disease, blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor B, wherein the other therapeutic agent is prepared for administration with a compound of formula (I). The invention also provides a compound of formula (I) for use in a method of treating a disease or condition mediated by the complement alternative pathway and/or Factor B, wherein the compound of formula (I) is administered with another therapeutic agent. The invention also provides another therapeutic agent for use in a method of treating a disease or condition mediated by the complement alternative pathway and/or Factor B, wherein the other therapeutic agent is administered with a compound of formula (I).

The invention also provides the use of a compound of formula (I) for treating a disease or condition mediated by the complement alternative pathway and/or Factor B, wherein the patient has previously (e.g. within 24 hours) been treated with another therapeutic agent. The invention also provides the use of another therapeutic agent for treating a disease or condition mediated by the complement alternative pathway and/or Factor B wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include complement inhibitors (such as inhibitors of Factor D, C5a receptor and antibody or Fabs against C5, C3, properidin, factor H, and the like), anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neurotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics. Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis Avastin and VEGF-R2 inhibitors including pazopanib, sutent, inifanib, and VEGF-R2 inhibitors disclosed in WO2010/066684) or photodynamic therapy (such as as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor B, wherein the method comprises administering to the subject a therapeutically effective amount of the compound according to the definition of Formula (I).

In one embodiment, the invention provides a compound according to the definition of formula I, II, or any subformulae thereof, for use as a medicament.

In one embodiment, the invention provides the use of a compound according to the definition of formula I, II, or any subformulae thereof, for the treatment of a disorder or disease in a subject mediated by complement activation. In particular, the invention provides the use of a compound according to the definition of formula I, II, or any subformulae thereof, for the treatment of a disorder or disease mediated by activation of the complement alternative pathway.

In one embodiment, the invention provides the use of a compound according to the definition of formula I, II, or a subformulae thereof in the manufacture of a medicament for the treatment of a disorder or disease in a subject characterized by activation of the complement system. More particularly in the manufacture of a medicament for the treatment of a disease or disorder in a subject characterized by over activation of the complement alternative pathway.

In one embodiment, the invention provides the use of a compound according to the definition of formula I, II, or subformulae thereof for the treatment of a disorder or disease in a subject characterized by activation of the complement system. More particularly, the invention provides uses of the compounds provided herein in the treatment of a disease or disorder characterized by over activation of the complement alternative pathway or the C3 amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing compelment mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

The following examples are intended to illustrate the invention and are not to be construed as being limitations thereon. Temperatures are given in degrees centrigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Inter Alia the following in vitro tests may be used

Biological Example 1: Human Complement Factor B ELISA Assay

CVF-Bb complex prepared from purified cobra venom factor (1 µM), recombinant human complement factor B (expressed in *drosophila* cells and purified using standard methods) and human complement factor D (expressed in *E. Coli*, refolded and purified using standard methods). CVF-Bb complex at 3 nM concentration was incubated with test compound at various concentrations for 1 hour at room temperature in PBS pH 7.4 containing 10 mM $MgCl_2$ and 0.05% (w/v) CHAPS. Human complement C3 substrate purified from plasma was added to a final concentration of 1 µM. After 1 hour incubation at room temperature, the enzyme reaction was stopped by addition of a cocktail of concentrated pan-protease inhibitors. The product of the reaction, C3a, was quantified by means of an enzyme-linked-immunosorbent assay. $IC_{50}$ values were calculated from percentage of inhibition of CVF-Bb activity as a function of test compound concentration.

Biological Example 2: Human Complement Factor B TR-FRET Assay

Biological Example 2.1: (+) or (−)-tert-Butyl 3-(3-hydroxyphenyl)piperazine-1-carboxylate

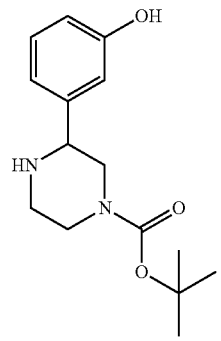 [SMILES: CC(C)(C)OC(=O)N1CCNC(c2cccc(O)c2)C1]

Resolution of the enantiomers of (±)-tert-butyl 3-(3-hydroxyphenyl)piperazine-1-carboxylate (CAS#889956-76-7) was achieved by chiral HPLC using a CHIRALPAK AD column with heptane/EtOAc/MeOH 90/5/5+0.1 diethylamine to give (+) or (−)-tert-butyl 3-(3-hydroxyphenyl)piperazine-1-carboxylate ($t_r$=9.7 min) and (−) or (+)-tert-butyl 3-(3-hydroxyphenyl)piperazine-1-carboxylate ($t_r$=15.7 min).

Biological Example 2.2: (+) or (−)-tert-Butyl 3-(3-(2-(((benzyloxy)carbonyl)amino)ethoxy)phenyl)piperazine-1-carboxylate

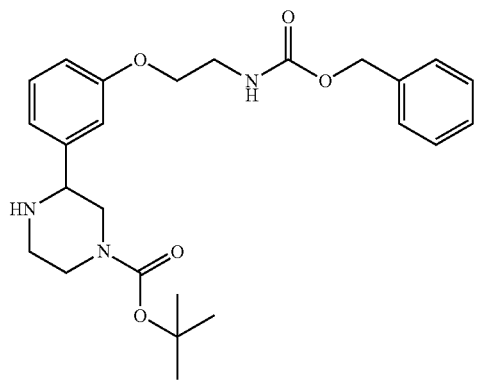 [SMILES: CC(C)(C)OC(=O)N1CCNC(c2cccc(OCCNC(=O)OCc3ccccc3)c2)C1]

(+) or (−)-tert-butyl 3-(3-hydroxyphenyl)piperazine-1-carboxylate (t$_r$=9.7 min) (Biological Example 2.1) (300 mg, 1.078 mmol) and benzyl 2-hydroxyethylcarbamate (210 mg, 1.078 mmol) were dissolved in THF (10 ml). Tributylphosphine (0.404 ml, 1.617 mmol) was added, and after cooling to 0° C., DEAD 40% in toluene (0.640 ml, 1.617 mmol) was added dropwise. The reaction was stirred for 2 h at 0° C., then overnight at rt. The reaction mixture was diluted with aqueous NaHCO$_3$. The layers were separated and the aqueous layer was extracted with AcOEt. The organic phase dried over MgSO$_4$ and concentrated in vacuum. The crude residue was purified by preparative HPLC (Macherey-Nagel Nucleosil 100-10 C18, CH$_3$CN/H$_2$O (0.1% TFA)) to give the title compound. MS (ESI+) m/z 455.2 (M+H).

Biological Example 2.3: (+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate

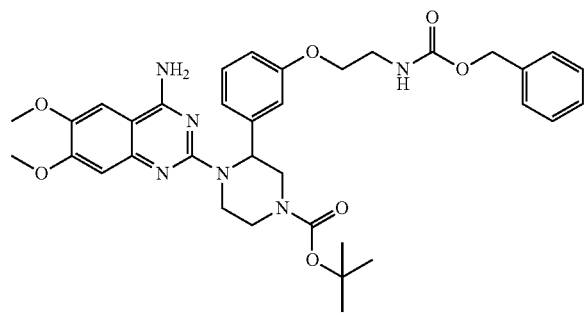 [SMILES: COc1cc2nc(N3CCN(C(=O)OC(C)(C)C)CC3c3cccc(OCCNC(=O)OCc4ccccc4)c3)nc(N)c2cc1OC]

A solution of 2-chloro-6,7-dimethoxyquinazolin-4-amine (CAS#23680-84-4) (105 mg, 0.439 mmol) and (+) or (−)-tert-butyl 3-(3-(2-(((benzyloxy)carbonyl)amino)ethoxy)phenyl)piperazine-1-carboxylate (100 mg, 0.220 mmol) in isoamyl alcohol (5 ml) was stirred for 16 hr at 135° C. After evaporation, the crude was purified by preparative HPLC (Macherey-Nagel Nucleosil® 100-10 C18, CH$_3$CN/H$_2$O (0.1% TFA)) to give the title compound. MS (ESI+) m/z 659.2 (M+H).

Biological Example 2.4: (+) or (−)-tert-Butyl ((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate

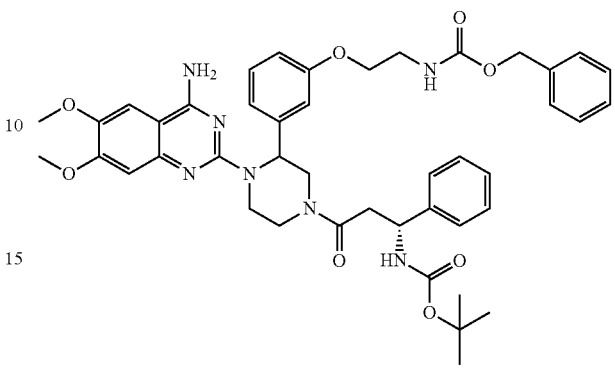

(+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate (60 mg, 0.078 mmol) was dissolved in 4N HCl in dioxane (5 ml) and stirred for 1 hr at rt. The reaction mixture was evaporated. The crude residue was dissolved in DMF (3 ml), and (R)-3-((tert-butoxycarbonyl)amino)-3-phenylpropanoic acid (21.0 mg, 0.079 mmol), DIPEA (0.041 ml, 0.238 mmol) and HATU (60.2 mg, 0.158 mmol) were added. The solution was stirred for 16 hr at rt. The reaction mixture was filtrated and evaporated in vacuum. The crude residue was purified by preparative HPLC (Waters SunFire™ Prep C18 OBD, CH$_3$CN/H$_2$O (0.1% TFA)) to give the title compound. MS (ESI+) m/z 806.2 (M+H).

Biological Example 2.5: (+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium

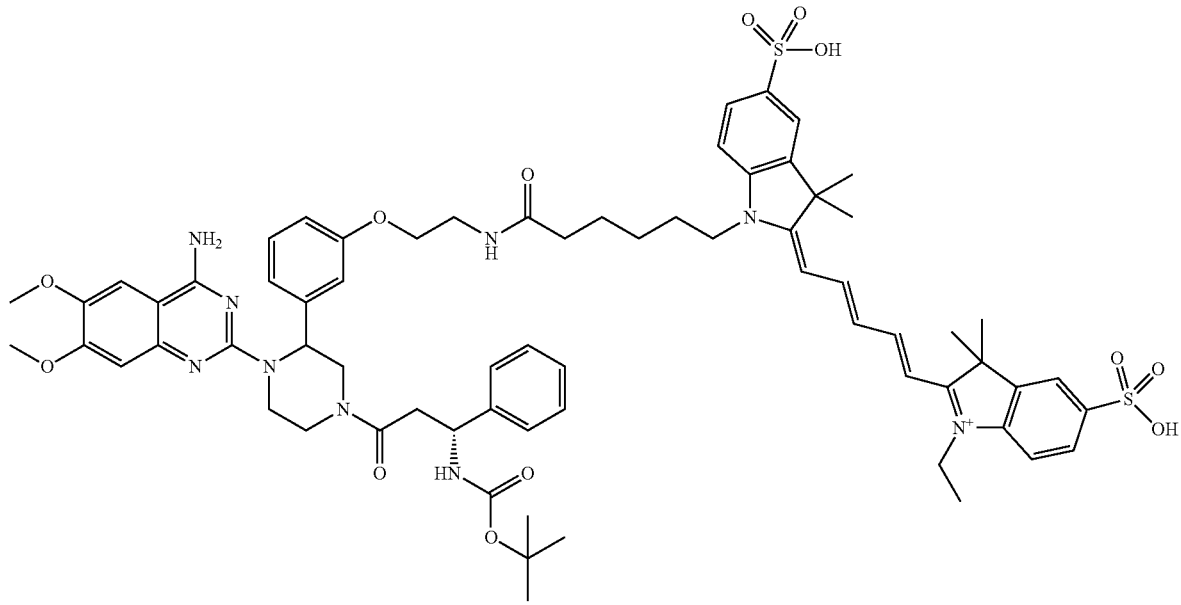 [SMILES: CC[N+]1=C(/C=C/C=C/C=C2/N(CCCCCC(=O)NCCOc3cccc(C4CN(C(=O)C[C@@H](NC(=O)OC(C)(C)C)c5ccccc5)CCN4c4nc(N)c5cc(OC)c(OC)cc5n4)c3)c3ccc(S(=O)(=O)O)cc3C2(C)C)C(C)(C)c2cc(S(=O)(=O)O)ccc21]

(+) or (−)-tert-Butyl ((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate (17 mg, 0.021 mmol) was dissolved in EtOH (5 ml), and added Pd/C (2.24 mg, 2.109 μmol). The reaction was stirred under $H_2$ for 16 hr at room temperature. The reaction mixture was filtered and evaporated. The resulting residue was dissolved in DMF (2 ml), and 2-((1E,3E,5E)-5-(1-(6-((2,5-dioxopyrrolidin-1-yl)oxy)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate (Cy-5, CAS#146368-14-1) (13.32 mg, 0.020 mmol), DIPEA (0.018 ml, 0.101 mmol) and HATU (15.40 mg, 0.040 mmol) were added. The solution stirred for 16 hr at rt. The reaction mixture evaporated in vacuum and purified by preparative HPLC (Macherey-Nagel Nucleosil® 100-10 C18, $CH_3CN/H_2O$ (0.1% TFA)) to give the title compound. MS (ESI+) m/z 656.1 (M/2).

Biological Example 2.6: (+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium

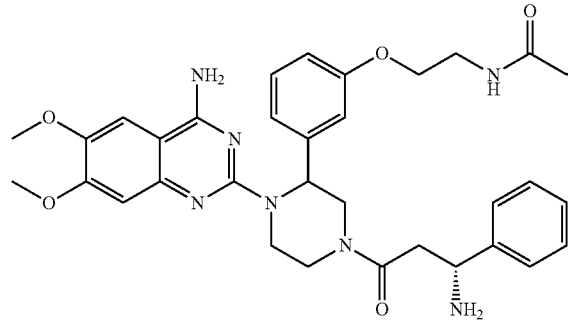
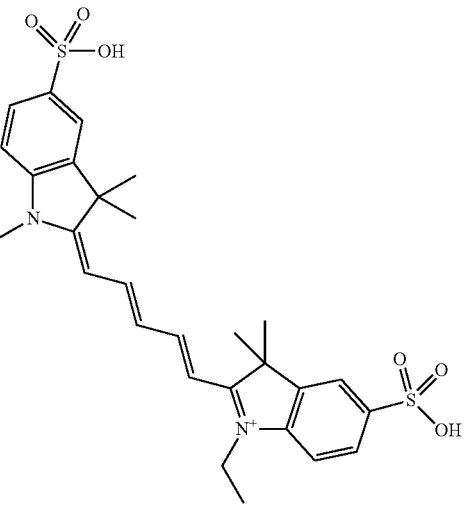

(+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (4 mg, 3.05 μmol) was dissolved in 4N HCl in dioxane (3 ml) and stirred for 1 hr at rt. The crude mixture was purified by preparative HPLC (Waters Sunfire™ C18 OBD, $CH_3CN/H_2O$ (0.1% TFA)) to give the title compound. Fractions were combined and evaporated to dryness. The residue was dissolved in a minimum amount of $CH_3CN$ and 1M aqueous HCl solution (3 ml, 3.00 mmol) was added. Mixture was then evaporated to give the title compound as HCl salt. $^1H$ NMR (HCl salt, 400 MHz, METHANOL-$d_4$) δ ppm 8.30 (m, 2H), 7.90 (s, 1H), 7.89 (d, J=5.4 Hz, 1H), 7.86 (d, J=5.6 Hz, 1H), 7.72 (dd, J=8.1, 37 Hz, 1H), 7.55 (d, J=7.2 Hz, 1H), 7.37-7.47 (m, 5H), 7.07-7.28 (m, 4H), 6.86-6.95 (m, 3H), 6.68 (t, J=12.5 Hz, 1H), 6.38 (dd, J=4.5, 18.4 Hz, 1H), 6.31 (d, J=13.9 Hz, 1H), 5.95 (br. s, 1H), 4.76-4.84 (m, 1H), 4.68-4.71 (m, 1H), 4.46-4.57 (m, 1H), 4.18-4.31 (m, 3H), 4.05-4.11 (m, 3H), 3.80-4.00 (m, 8H), 3.41-3.60 (m, 3H), 3.06-3.09 (m, 2H), 2.84 (dd, J=3.8, 22.5 Hz, 1H), 2.12-2.22 (m, 2H), 1.75-1.86 (m, 2H), 1.73 (s, 6H), 1.70 (s, 6H), 1.59-1.69 (m, 2H), 1.39 (t, J=7.3 Hz, 3H), 1.29-1.37 (m, 2H). UPLC-MS (ESI+) m/z 606.1 (M/2); Instrument: Waters UPLC Acquity; column: Acquity HSS T3 1.8 μm 2.1×50 mm at 50° C., eluent A: water+0.05% HCOOH+3.75 mM ammonium acetate, B: $CH_3CN$+0.04% HCOOH, Gradient: 5 to 98% B in 1.4 min, flow: 1.0 ml/min; Retention time: 0.64 min.

Biological Example 2.7

Recombinant human factor B (expressed in *drosophila* cells and purified using standard methods) labeled with biotin (10 nM), europium-labeled streptavidin (5 nM) and (+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) (75 nM) were incubated with test compound at various concentrations up to 2 hours at room temperature in 20 mM Tris/HCl, pH 7.4, 0.005% (v/v) Tween20.

The time-gated decrease in fluorescence intensity related to the competition between labeled and unlabeled factor B ligands was recorded at both 620 nm and 665 nm, 70 μs after excitation at 337 nm using a microplate spectrofluorimeter. $IC_{50}$ values were calculated from percentage of inhibition of complement factor B-(+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) displacement as a function of test compound concentration.

The following Examples, while representing preferred embodiments of the invention, serve to illustrate the invention without limiting its scope.

ABBREVIATIONS

Ac acetyl
AcOH acetic acid
app apparent
aq. aqueous
atm atmosphere
Boc tertiary butyl carboxy
br. broad
BuOH butanol
calcd. calculated
CHAPS 3-[(3-cholamidopropyl)dimethylammonio]-1-propanesulfonate
CVF Cobra Venom Factor
d doublet
dd doublet of doublets
DMF N,N-dimethylformamide
DMSO dimethylsulfoxide
ESI electrospray ionization
EtOAc ethyl acetate
Et ethyl
EtOH ethanol
g grams
h hour(s)
HC HPLC condition
HFIP 1,1,1,3,3,3-hexafluoro-2-propanol
HPLC high performance liquid chromatography
IR infrared spectroscopy
L litter(s)
LDA lithium diisopropyl amide
TMP 2,2',6,6'-tetramethylpiperidine, 2,2',6,6'-tetramethylpiperidyl
M molar
MHz mega Herts
m multiplet
Me methyl
MeI iodomethane
MeOH methanol
mg milligram(s)
mm millimeter (s)
min minutes
mL milliliter(s)
mmol millimoles
MS mass spectrometry
m/z mass to charge ratio
N normal
NMR nuclear magnetic resonance
PBS phosphate buffered saline
Pd/C palladium on carbon
Ph phenyl
ppm parts per million
rac racemic
RP—reverse phase
rt room temperature
$t_r$ retention time
s singlet
sat. saturated
SEM 2-(trimethylsilyl)ethoxymethyl
SFC Supercritical Fluid Chromatography
t triplet
TBAF tetra-n-butylammonium fluoride
TEA, $Et_3N$ triethylamine
tert—tertiary
TFA trifluoroacetic acid
TFAA trifluoroacetic anhydride
THF tetrahydrofuran
TMS trimethylsilyl
Ts p-toluenesulfonyl
TsOH p-toluenesulfonic acid
v/v volume per volume
w/v weight per volume The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu.

Following preparation methods were used for RP-HPLC.

HC-A:

Stationary phase: Waters SunFire™ Prep C18 OBD™ 5 μm, 30×100 mm

Mobile phase: gradient, water with 0.1% TFA/acetonitrile

HC-B

Stationary phase: Gemini® NX 5μ C18 110A 100×30 mm

Mobile phase: gradient, water with 0.1% (28% ammonium hydroxide)/acetonitrile

Intermediate 1:
2-Methoxy-4,6-dimethylbenzaldehyde

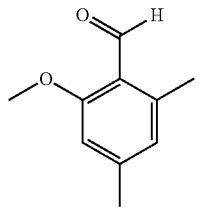

To a solution of 2-hydroxy-4,6-dimethylbenzaldehyde (CAS#1666-02-0, 100 mg, 0.666 mmol) and MeI (0.083 ml, 1.332 mmol) in DMF (5 ml) was added NaH (53.3 mg, 1.332 mmol). The mixture was then stirred at room temperature for 1.5 h, and then poured into ice. The mixture mixture was extracted with Et$_2$O. The organic layer was then washed successively with H$_2$O and brine, dried over Na$_2$SO$_4$, filtered, and then concentrated to furnish the title compound. MS (ESI+) m/z 165.0 (M+H).

Intermediate 2: 2-Methoxy-4-methylbenzaldehyde

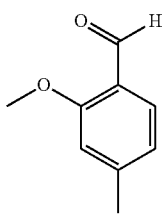

The title compound was synthesized from 2-hydroxy-4-methylbenzaldehyde (CAS#698-27-1) analogously to Intermediate 1. $^1$H NMR (400 MHz, CD$_2$Cl$_2$) δ 10.37 (d, J=0.63 Hz, 1H), 7.67 (d, J=7.71 Hz, 1H), 6.82-6.87 (m, 2H), 3.91 (s, 3H), 2.41 (s, 3H).

Intermediate 3:
3-Chloro-6-methoxy-2,4-dimethylbenzaldehyde

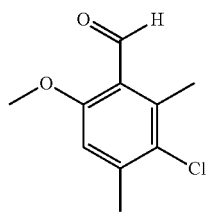

The title compound was synthesized from 3-chloro-6-hydroxy-2,4-dimethylbenzaldehyde (CAS#88174-46-3) analogously to Intermediate 1. MS (ESI+) m/z 199.0 (M+H).

Intermediate 4

Intermediate 4-A:
(2-Methoxy-6-methylphenyl)methanol

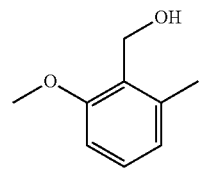

To a solution of methyl 2-methoxy-6-methylbenzoate (CAS#79383-44-1, 500 mg, 2.77 mmol) in THF (5 ml) at 0° C. was added LiAlH$_4$ (211 mg, 5.55 mmol). The mixture was stirred at 0° C. for 2 h and then at room temperature for 15 h. The reaction mixture was then diluted with THF, and then quenched with sodium sulfate decahydrate. The mixture was then stirred for 1 h, dried over Na$_2$SO$_4$, filtered, and then concentrated to furnish the title compound. MS (ESI+) m/z 135.0 (M-OH).

Intermediate 4-B:
2-Methoxy-6-methylbenzaldehyde

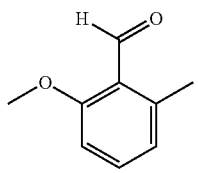

A mixture of (2-methoxy-6-methylphenyl)methanol (350 mg, 2.300 mmol) and MnO$_2$ (4 g, 46.0 mmol) in CH$_2$Cl$_2$ (10 ml) was stirred at 45° C. for 3 days, and then cooled to room temperature. The mixture was filtered through a plug of Celite®, which was rinsed with CH$_2$Cl$_2$. The filtrate was concentrated to furnish the title compound. MS (ESI+) m/z 150.9 (M+H).

Intermediate 5

Intermediate 5-A:
3-Bromo-6-hydroxy-2,4-dimethylbenzaldehyde

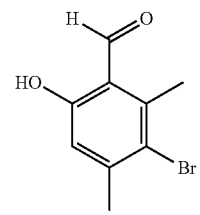

To a solution of 4-bromo-3,5-dimethylphenol (CAS#7463-51-6, 6 g, 29.8 mmol) in CHCl$_3$ (150 ml) was added a 35% aq. solution of NaOH (100 ml, 29.8 mmol) slowly. The mixture was then stirred at 70° C. for 8 h. The reaction mixture was cooled to 0° C., and then poured into ice. The mixture was rendered acidic by 12N HCl until pH<4. The mixture was then added NaHCO₃ until the aqueous media became pH around 7. The reaction mixture was then extracted with three times with CH₂Cl₂. The combined organic layer was then washed successively with brine, dried over Na₂SO₄, filtered, and then concentrated. The resulting residue was purified by silica gel flash column chromatography (CH₂Cl₂/EtOAc=1/0 to 6/4) to afford the title compound. MS (ESI+) m/z 229.0 (M+H).

Intermediate 5-B:
3-Bromo-6-methoxy-2,4-dimethylbenzaldehyde

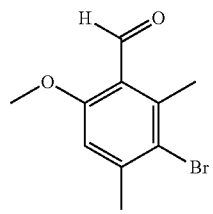

The title compound was synthesized from 3-bromo-6-hydroxy-2,4-dimethylbenzaldehyde analogously to Intermediate 1. MS (ESI+) m/z 242.9 (M+H).

Example 1

Example 1-A: 1-((2-(Trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile

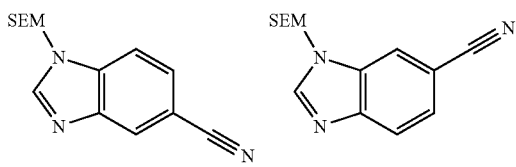 [SMILES: C[Si](C)(C)CCOCn1cnc2cc(C#N)ccc21 ; C[Si](C)(C)CCOCn1cnc2ccc(C#N)cc21]

To a solution of 1H-benzo[d]imidazole-5-carbonitrile (CAS#; 6287-83-8) (1 g, 3.81 mmol) in DMF (50 mL) was added NaH (60% in mineral oil, 610 mg, 15.3 mmol), and then the mixture was stirred at room temperature for 1 h, and then cooled down to 0° C. SEMCl (0.75 mL, 4.2 mmol) was then added at 0° C., and then the mixture was stirred at 0° C. for 0.5 h. The reaction was quenched with MeOH at 0° C. and then diluted with Et₂O. The layers were separated and the organic layer was washed successively with H₂O and brine, it was then dried over Na₂SO₄, filtered and concentrated. The resulting residue was purified by silica gel flash chromatography (10-20% EtOAc in CH₂Cl₂) to afford a mixture of the title compounds, which was used in the next step without further purification. MS (ESI+) m/z 274.3 (M+H).

Example 1-B: (±)-2-(Hydroxy(2-methoxy-4,6-dimethylphenyl)methyl)-1-((2-(trimethylsilyl)ethoxy)methyl)-1H-benzo[d]imidazole-5-carbonitrile and (±)-2-(hydroxy(2-methoxy-4,6-dimethylphenyl)methyl)-1-((2-(trimethylsilyl)ethoxy)methyl)-1H-benzo[d]imidazole-6-carbonitrile To a solution of a mixture of 1-((2-(trimethylsilyl)ethoxy)methyl)-1H-benzo[d]imidazole-5-carbonitrile and 2-(hydroxy(2-methoxy-4,6-dimethylphenyl)methyl)-1-((2-(trimethylsilyl)ethoxy)methyl)-1H-benzo[d]imidazole-6-carbonitrile (272 mg, 0.996 mmol) in THF (4 ml) was added LDA in THF/ethylbenzene/n-hexane (2M, 0.553 ml, 0.996 mmol) at −78° C. The mixture was then stirred at −78° C. for 0.5 h. To the mixture was then added a solution of 2-methoxy-4,6-dimethylbenzaldehyde (Intermediate 1) (109 mg, 0.664 mmol) in THF (2 ml) at −78° C. The mixture was then stirred at −78° C. for 45 min, and then quenched with MeOH. The mixture was warmed up to room temperature. The mixture was diluted with CH₂Cl₂. The organic phase was washed successively with H₂O and brine, dried over Na₂SO₄, filtered, and then concentrated to furnish a mixture of the title compounds. MS (ESI+) m/z 438.0 (M+H).

Example 1-C: (±)-2-(Hydroxy(2-methoxy-4,6-dimethylphenyl)methyl)-1H-benzo[d]imidazole-5-carbonitrile

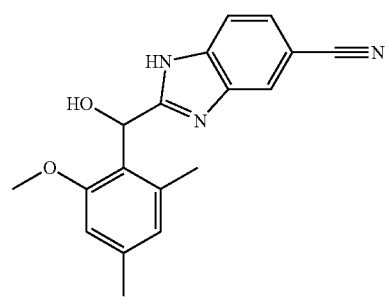 [SMILES: COc1cc(C)cc(C)c1C(O)c1nc2cc(C#N)ccc2[nH]1]

A solution of a mixture of (±)-2-(hydroxy(2-methoxy-4,6-dimethylphenyl)methyl)-1-((2-(trimethylsilyl)ethoxy)methyl)-1H-benzo[d]imidazole-5-carbonitrile and (±)-2-(hydroxy(2-methoxy-4,6-dimethylphenyl)methyl)-1-((2-(trimethylsilyl)ethoxy)methyl)-1H-benzo[d]imidazole-6-carbonitrile (80 mg, 0.132 mmol) in 1M HCl in MeOH (1 ml) was stirred at 65° C. for 22.5 h. The mixture was then cooled to room temperature, and then diluted with $CH_2Cl_2$. The mixture was washed successively with 5% aq. $NaHCO_3$, $H_2O$ and brine, dried over $Na_2SO_4$, filtered, and then concentrated. The resulting residue was purified by RP-HPLC (HC-A) to afford the title compound. $^1$H NMR (with ~5 µL TFA, 400 MHz, $CD_3CN$) δ 7.94 (s, 1H) 7.67 (d, J=8.34 Hz, 1H) 7.56 (dd, J=8.30, 1.30 Hz, 1H) 6.70 (br. s, 1H) 6.63 (s, 1H) 6.37 (s, 1H) 3.62 (s, 3H) 2.28 (s, 3H) 2.25 (s, 3H). HRMS; calcd. for $C_{18}H_{18}N_3O_2$ 308.1399 (M+H). found 308.1397.

Example 2

Example 2-A: 2-(2-Methoxy-4,6-dimethylbenzoyl)-1-((2-(trimethylsilyl)ethoxy)methyl)-1H-benzo[d]imidazole-5-carbonitrile and 2-(2-methoxy-4,6-dimethylbenzoyl)-1-((2-(trimethylsilyl)ethoxy)methyl)-1H-benzo[d]imidazole-6-carbonitrile

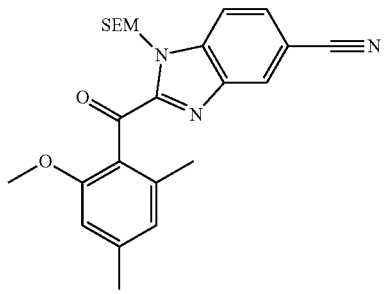

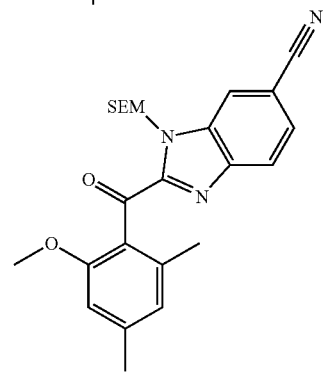

A mixture of (±)-2-(2-methoxy-4,6-dimethylbenzoyl)-1-((2-(trimethylsilyl)ethoxy)methyl)-1H-benzo[d]imidazole-5-carbonitrile and (±)-2-(2-methoxy-4,6-dimethylbenzoyl)-1-((2-(trimethylsilyl)ethoxy)methyl)-1H-benzo[d]imidazole-6-carbonitrile (Example 1-B) (320 mg, 0.527 mmol) and $MnO_2$ (915 mg, 10.53 mmol) in $CH_2Cl_2$ (5 ml) was stirred at 45° C. for 5 h, and then cooled to room temperature. The reaction mixture was filtered through a plug of Celite®, which was rinsed with $CH_2Cl_2$. The filtrate was concentrated to furnish a mixture of the title compounds. MS (ESI+) m/z 436.2 (M+H).

Example 2-B: (±)-2-(Hydroxy(2-methoxy-4,6-dimethylphenyl)methyl)-1-((2-(trimethylsilyl)ethoxy)methyl)-1H-benzo[d]imidazole-5-carbonitrile and (±)-2-(1-hydroxy-1-(2-methoxy-4,6-dimethylphenyl)ethyl)-1-((2-(trimethylsilyl)ethoxy)methyl)-1H-benzo[d]imidazole-6-carbonitrile

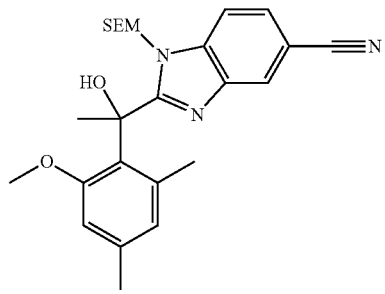

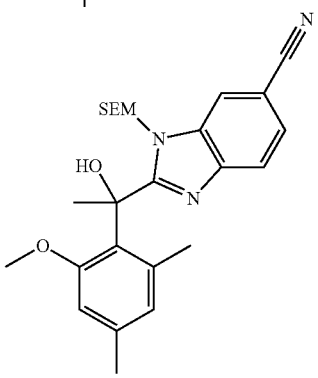

To a solution of a mixture of 2-(2-methoxy-4,6-dimethylbenzoyl)-1-((2-(trimethylsilyl)ethoxy)methyl)-1H-benzo[d]imidazole-5-carbonitrile and 2-(2-methoxy-4,6-dimethylbenzoyl)-1-((2-(trimethylsilyl)ethoxy)methyl)-1H-benzo[d]imidazole-6-carbonitrile (80 mg, 0.156 mmol) in THF (2 ml) at 0° C. was added MeMgI in $Et_2O$ (0.104 ml, 0.312 mmol). The mixture was then stirred at 0° C. for 1 h, and then quenched with half satd. aq. $KHSO_4$. The mixture was extracted with $CH_2Cl_2$. The organic phase was successively washed with $H_2O$ and brine, dried over $Na_2SO_4$, filtered, and concentrated to furnish a mixture of the title compounds. MS (ESI+) m/z 452.2 (M+H).

Example 2-C: (±)-2-(1-Hydroxy-1-(2-methoxy-4,6-dimethylphenyl)ethyl)-1H-benzo[d]imidazole-5-carbonitrile

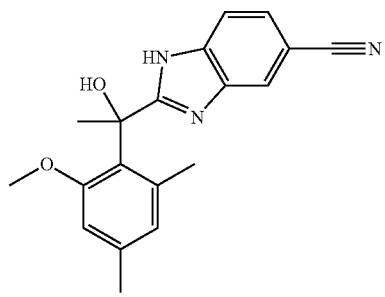 [SMILES: COc1cc(C)cc(C)c1C(C)(O)c1nc2cc(C#N)ccc2[nH]1]

To a solution of a mixture of (±)-2-(hydroxy(2-methoxy-4,6-dimethylphenyl)methyl)-1-((2-(trimethylsilyl)ethoxy)methyl)-1H-benzo[d]imidazole-5-carbonitrile and (±)-2-(1-hydroxy-1-(2-methoxy-4,6-dimethylphenyl)ethyl)-1-((2-(trimethylsilyl)ethoxy)methyl)-1H-benzo[d]imidazole-6-carbonitrile (70 mg, 0.155 mmol) and ethylenediamine (0.105 ml, 1.550 mmol) in THF (1 mL) was added TBAF in THF (1.550 ml, 1.550 mmol). The mixture was then stirred at 60° C. for 14 h and then diluted with EtOAc. The mixture was washed successively with 5% aq. NaHCO$_3$, H$_2$O and brine, dried over Na$_2$SO$_4$, filtered, and then concentrated. The resulting residue was purified by RP-HPLC (HC-A) to afford the title compound. $^1$H NMR (with ~5 μL TFA, 400 MHz, CD$_3$CN) δ 8.03 (s, 1H) 7.70 (d, J=8.60 Hz, 1H) 7.64 (dd, J=8.60, 1.50 Hz, 1H) 6.66 (s, 1H) 6.65 (s, 1H) 3.36 (s, 3H) 2.37 (s, 3H) 2.26 (s, 3H) 2.02 (s, 3H). HRMS; calcd. for C$_{18}$H$_{19}$N$_4$O 322.1556 (M+H). found 322.1554.

Example 3

Example 3-A: (±)-2-(2,2,2-Trifluoro-1-hydroxy-1-(2-methoxy-4,6-dimethylphenyl)ethyl)-1-((2-(trimethylsilyl)ethoxy)methyl)-1H-benzo[d]imidazole-5-carbonitrile and (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-6-carbonitrile

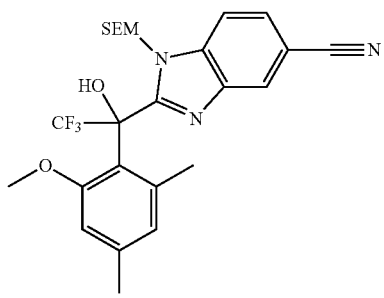

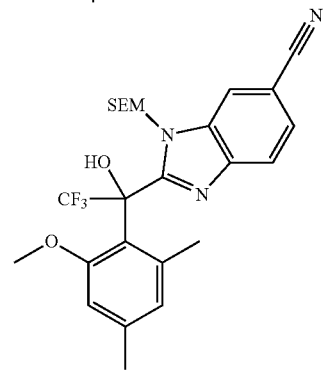

To a solution of a mixture of 2-(2-methoxy-4,6-dimethylbenzoyl)-1-((2-(trimethylsilyl)ethoxy)methyl)-1H-benzo[d]imidazole-5-carbonitrile and 2-(2-methoxy-4,6-dimethylbenzoyl)-1-((2-(trimethylsilyl)ethoxy)methyl)-1H-benzo[d]imidazole-6-carbonitrile (Example 2-A) (200 mg, 0.390 mmol) and trimethyl(trifluoromethyl)silane (0.122 ml, 0.781 mmol) in THF (2 ml) was added TBAF in THF (1M, 1.17 mL, 1.17 mmol) dropwise at room temperature. The mixture was then stirred at room temperature for 1 h, and then diluted with CH$_2$Cl$_2$. The mixture was washed successively with 5% aq. NaHCO$_3$, H$_2$O and brine, dried over Na$_2$SO$_4$, filtered, and then concentrated to furnish a mixture of the title compounds. MS (ESI+) m/z 506.2 (M+H).

Example 3-B: (±)-2-(2,2,2-Trifluoro-1-hydroxy-1-(2-methoxy-4,6-dimethylphenyl)ethyl)-1H-benzo[d]imidazole-5-carbonitrile

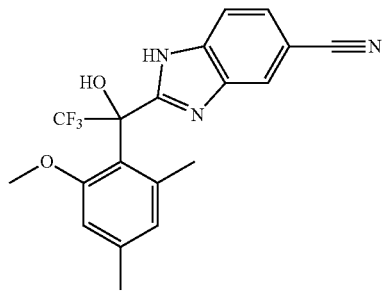 [SMILES: COc1cc(C)cc(C)c1C(O)(c1nc2cc(C#N)ccc2[nH]1)C(F)(F)F]

The title compound was synthesized from a mixture of (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-5-carbonitrile and (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-6-carbonitrile analogously to Example 1-C. $^1$H NMR (with ~5 μL TFA, 400 MHz, CD$_3$CN) δ 8.05 (s, 1H) 7.68 (d, J=8.30 Hz, 1H) 7.60 (dd, J=8.30, 1.50 Hz, 1H) 6.82 (s, 1H) 6.71 (s, 1H) 6.89 (br. s, 1H) 3.58 (s, 3H) 2.29 (s, 3H) 1.99 (s, 3H). HRMS; calcd. for C$_{16}$H$_{17}$N$_3$O$_2$F$_3$ 376.1273 (M+H). found 376.1285.

Example 4: (±)-2-(1-(3-bromo-6-methoxy-2,4-dimethylphenyl)-2,2,2-trifluoro-1-hydroxyethyl)-1H-benzo[d]imidazole-5-carbonitrile

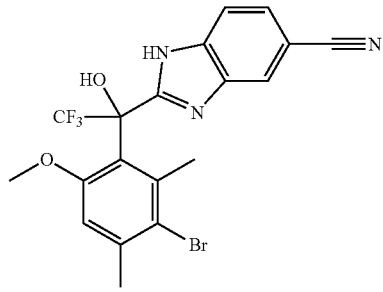 [SMILES: COc1cc(C)c(Br)c(C)c1C(O)(c1nc2cc(C#N)ccc2[nH]1)C(F)(F)F]

The title compound was synthesized from a mixture of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (Example 1-A) and 3-bromo-6-methoxy-2,4-dimethylbenzaldehyde (Intermediate 5-B) analogously to Example 3. $^1$H NMR (TFA salt, 400 MHz, DMSO-d$_6$) δ 8.08 (br. s., 1H), 7.77 (br. s., 1H), 7.59-7.68 (m, 1H), 7.56 (dd, J=1.50, 8.30 Hz, 1H), 6.94 (s, 1H), 3.06 (s, 3H), 2.68 (s, 3H), 2.39 (s, 3H). HRMS; calcd. for C$_{16}$H$_{16}$BrF$_3$N$_3$O$_2$ 454.0378 (M+H). found 454.0377.

Example 5: a) (±)-2-(2,2,2-Trifluoro-1-(2-methoxy-4,6-dimethylphenyl)-1-(methylamino)ethyl)-1H-benzo[d]imidazole-5-carbonitrile

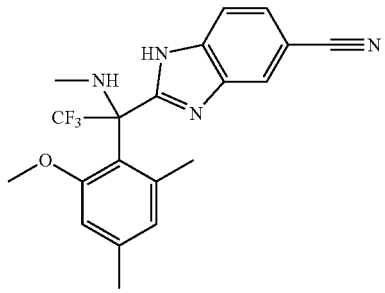 [SMILES: CNC(c1nc2cc(C#N)ccc2[nH]1)(c1c(C)cc(C)cc1OC)C(F)(F)F]

To a solution of (±)-2-(2,2,2-trifluoro-1-hydroxy-1-(2-methoxy-4,6-dimethylphenyl)ethyl)-1H-benzo[d]imidazole-5-carbonitrile (54 mg, 0.144 mmol) (Example 3-B) and DMF (5 μL) in CHCl$_3$ was added thionyl chloride (0.105 mL, 1.439 mmol). The mixture was then stirred at 75° C. for 2 h, and then concentrated to dryness. To the resulting residue was then added 33% methylamine in EtOH (3 ml, 0.144 mmol). The mixture was then stirred at room temperature for 1 h, and then concentrated to the half volume, and then diluted with CH$_2$Cl$_2$. The mixture was washed with sat aq. NaHCO$_3$, dried over Na$_2$SO$_4$, filtered, and then concentrated. The resulting residue was purified by silica gel flash column chromatography to afford the title compound. $^1$H NMR (400 MHz, CD$_2$Cl$_2$) δ 8.17 (s, 1H), 7.82 (d, J=8.21 Hz, 1H), 7.70 (dd, J=1.45, 8.53 Hz, 1H), 6.81 (s, 1H), 6.71 (s, 1H), 3.93 (s, 3H), 2.64 (s, 3H), 2.33 (s, 3H), 1.48 (s, 3H). HRMS; calcd. for C$_{20}$H$_{20}$F$_3$N$_3$O$_2$ 389.1589. found 389.1588.

b) (+) or (−)-2-(2,2,2-Trifluoro-1-(2-methoxy-4,6-dimethylphenyl)-1-(methylamino)ethyl)-1H-benzo[d]imidazole-5-carbonitrile and (−) or (+)-2-(2,2,2-Trifluoro-1-(2-methoxy-4,6-dimethylphenyl)-1-(methylamino)ethyl)-1H-benzo[d]imidazole-5-carbonitrile Resolution of the enantiomers (±)-2-(2,2,2-trifluoro-1-(2-methoxy-4,6-dimethylphenyl)-1-(methylamino)ethyl)-1H-benzo[d]imidazole-5-carbonitrile was achieved by chiral SFC using a AD-H column with 10% iPrOH in CO$_2$ to give (+) or (−)-(±)-2-(2,2,2-trifluoro-1-(2-methoxy-4,6-dimethylphenyl)-1-(methylamino)ethyl)-1H-benzo[d]imidazole-5-carbonitrile (t$_r$=3.7 min) and (−) or (+)-(±)-2-(2,2,2-trifluoro-1-(2-methoxy-4,6-dimethylphenyl)-1-(methylamino)ethyl)-1H-benzo[d]imidazole-5-carbonitrile (t$_r$=4.7 min).

Example 6

The following compounds were prepared with similar method as described in Example 5 using the appropriate aldehydes.

| | Structure/Chemical Name | $^1$H NMR | HRMS |
|---|---|---|---|
| 6-A | (±)-2-(2,2,2-Trifluoro-1-(2-methoxy-4-methylphenyl)-1-(methylamino)ethyl)-1H-benzo[d]imidazole-5-carbonitrile | (TFA salt, 400 MHz, DMSO-d$_6$) δ 8.10 (br. s., 1H), 7.67 (br. d, J = 8.28 Hz, 1H), 7.58 (dd, J = 1.52, 8.28 Hz, 1H), 7.29 (d, J = 7.83 Hz, 1H), 6.91 (s, 1H), 6.89 (d, J = 8.08 Hz, 1H), 3.35 (s, 3H), 2.33 (s, 3H), 2.15 (s, 3H). | calcd. for (M + H), C$_{19}$H$_{18}$F$_3$N$_4$O calcd. 375.1433, found 375.1436. |
| 6-B | (±)-2-(1-(3-Chloro-6-methoxy-2,4-dimethylphenyl)-2,2,2-trifluoro-1-(methylamino)ethyl)-1H-benzo[d]imidazole-5-carbonitrile | (with ~5 μL TFA, 400 MHz, CD$_3$CN) δ 8.06 (s, 1H), 7.68 (d, J = 8.60 Hz, 1H), 7.59 (dd, J = 1.50, 8.60 Hz, 1H), 6.98 (s, 1H), 3.63 (s, 3H), 2.39 (s, 3H), 2.19 (s, 3H), 2.02 (br. s, 3H) | calcd. for (M + H), C$_{20}$H$_{19}$ClF$_3$N$_4$O calcd. 423.1199, found 423.1201 |

| Structure/Chemical Name | ¹H NMR | HRMS |
|---|---|---|
| 6-C 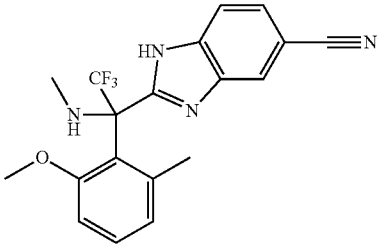 [SMILES: CNC(c1nc2cc(C#N)ccc2[nH]1)(c1c(C)cccc1OC)C(F)(F)F] (±)-2-(2,2,2-Trifluoro-1-(2-methoxy-6-methylphenyl)-1-(methylamino)ethyl)-1H-benzo[d]imidazole-5-carbonitrile | (with ~5 μL TFA, 400 MHz, $CD_3CN$) δ 10.90 (br. s., 1H), 8.01 (br. s., 1H), 7.64 (br. s., 1H), 7.55 (dd, J = 1.52, 8.34 Hz, 1H), 7.28 (dd, J = 7.60, 8.00 Hz, 1H), 6.92 (d, J = 8.10 Hz, 1H), 6.84 (dd, J = 0.63, 7.71 Hz, 1H), 3.48 (s, 3H), 2.03-2.24 (m, 6H). | calcd. for (M + H), $C_{19}H_{18}F_3N_4O$ calcd. 375.1433, found 375.1441 |
| 6-D 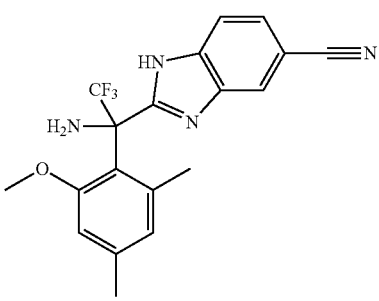 [SMILES: COc1cc(C)cc(C)c1C(N)(c1nc2cc(C#N)ccc2[nH]1)C(F)(F)F] (±)-2-(1-Amino-2,2,2-trifluoro-1-(2-methoxy-4,6-dimethylphenyl)ethyl)-1H-benzo[d]imidazole-5-carbonitrile (28% aq. $NH_4OH$ was used in the place of 33% $MeNH_2$ in EtOH) | (400 MHz, $CD_3CN$) δ 8.10 (s, 1H), 7.72 (d, J = 8.30 Hz, 1H), 7.64 (dd, J = 1.50, 8.30 Hz, 1H), 6.83 (s, 1H), 6.67 (s, 1H), 3.72 (s, 3H), 2.27 (s, 3H), 1.70 (s, 3H) | HRMS; calcd. for $C_{19}H_{18}F_3N_4O$ 375.1433 (M + H), found 375.1427. |
| 6-E 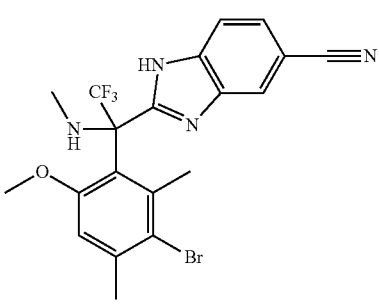 [SMILES: CNC(c1nc2cc(C#N)ccc2[nH]1)(c1c(OC)cc(C)c(Br)c1C)C(F)(F)F] (±)-2-(1-(3-Bromo-6-methoxy-2,4-dimethylphenyl)-2,2,2-trifluoro-1-(methylamino)ethyl)-1H-benzo[d]imidazole-5-carbonitrile | (400 MHz, $CD_3OD$) δ 8.01 (s, 1H), 7.71 (d, J = 8.46 Hz, 1H), 7.61 (dd, J = 1.45, 8.40 Hz, 1H), 6.99 (s, 1H), 3.51 (s, 3H), 2.46 (s, 3H), 2.38 (br. s., 3H), 2.25 (s, 3H) | calcd. for $C_{20}H_{19}BrF_3N_4O$ 467.0694 (M + H), found 467.0676 |

Example 7

Example 7-A: (±)-N-((5-Cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide and (±)-N-((6-cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide

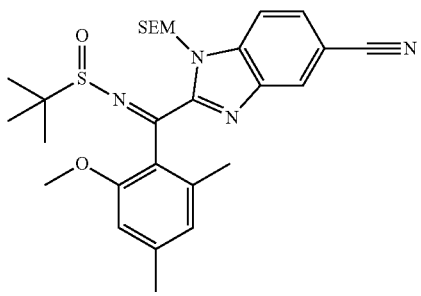

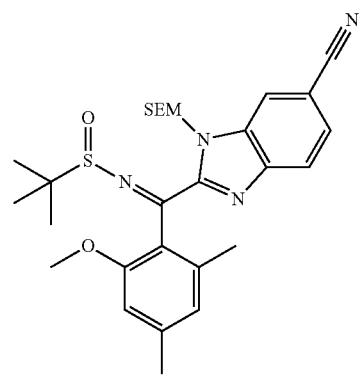

A suspension of a mixture of 2-(2-methoxy-4,6-dimethylbenzoyl)-1-((2-(trimethylsilyl)ethoxy)methyl)-1H-benzo[d]imidazole-5-carbonitrile and 2-(2-methoxy-4,6-dimethylbenzoyl)-1-((2-(trimethylsilyl)ethoxy)methyl)-1H-benzo[d]imidazole-6-carbonitrile (Example 2-A) (1.742 g, 4 mmol), Zr(O-tBu)₄ (0.5M in toluene, 6.4 mL, 16 mmol), and (±)-2-methylpropane-2-sulfinamide (0.970 g, 8.00 mmol) in toluene (20 ml) was stirred at 100° C. for 4 h. To the mixture was added additional amount of Zr(O-tBu)₄ (0.5M in toluene, 6.4 mL, 16 mmol). The mixture was then stirred at the same temperature for 1 h, and then diluted with CH₂Cl₂. To the mixture was added Celite®, followed by H₂O. The whole mixture was then stirred at room temperature for 0.5 h. The mixture was filtered through a plug of Celite®, which was rinsed with CH₂Cl₂. The organic layer was washed successively with H₂O and brine, dried over Na₂SO₄, filtered, and then concentrated to furnish a mixture of the title compounds. MS (ESI+) m/z 539.2 (M+H).

Example 7-B: (±)-N-((5-Cyano-1-((2-(trimethylsilyl)ethoxy)methyl)-1H-benzo[d]imidazol-2-yl)(2-methoxy-4,6-dimethylphenyl)methyl)-2-methylpropane-2-sulfinamide and (±)-N-((6-cyano-1-((2-(trimethylsilyl)ethoxy)methyl)-1H-benzo[d]imidazol-2-yl)(2-methoxy-4,6-dimethylphenyl)methyl)-2-methylpropane-2-sulfinamide

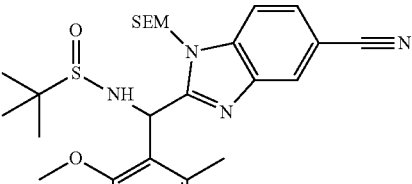

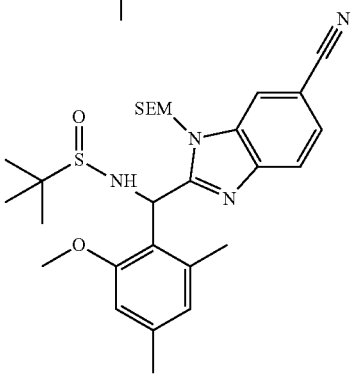

To a solution of a mixture of (±)-N-((5-cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide and (±)-N-((6-cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide (1.078 g, 2 mmol) in MeOH (30 ml) at 0° C. was added NaBH₄ (0.757 g, 20 mmol). The mixture was then stirred at room temperature for 1 h, and then diluted with H₂O and CH₂Cl₂. The organic layer was washed successively with H₂O and brine, dried over Na₂SO₄, filtered, and then concentrated to furnish a mixture of the title compounds. MS (ESI+) m/z 541.2 (M+H).

Example 7-C: (±)-2-(Amino(2-methoxy-4,6-dimethylphenyl)methyl)-1-((2-(trimethylsilyl)ethoxy)methyl)-1H-benzo[d]imidazole-5-carbonitrile and (±)-2-(amino(2-methoxy-4,6-dimethylphenyl)methyl)-1-((2-(trimethylsilyl)ethoxy)methyl)-1H-benzo[d]imidazole-6-carbonitrile

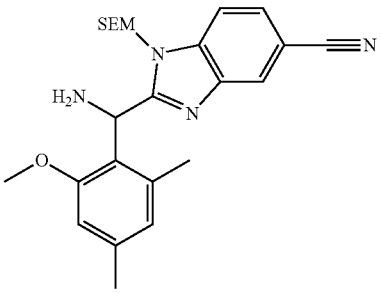

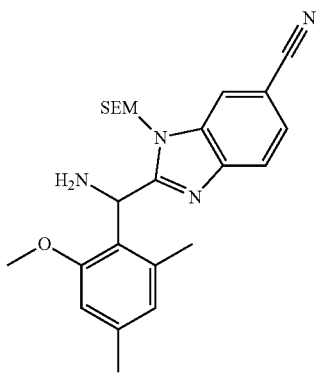

A mixture of (±)-N-((5-cyano-1-((2-(trimethylsilyl)ethoxy)methyl)-1H-benzo[d]imidazol-2-yl)(2-methoxy-4,6-dimethylphenyl)methyl)-2-methylpropane-2-sulfinamide and (±)-N-((6-cyano-1-((2-(trimethylsilyl)ethoxy)methyl)-1H-benzo[d]imidazol-2-yl)(2-methoxy-4,6-dimethylphenyl)methyl)-2-methylpropane-2-sulfinamide (1.082 g, 2 mmol) and 1M HCl in MeOH (20 ml) was stirred at room temperature for 3 h, and then diluted with CH₂Cl₂. The organic layer was washed successively with 5% aq. NaHCO₃, H₂O and brine, dried over Na₂SO₄, filtered, and concentrated. The resulting residue was purified by silica gel flash column chromatography [CH₂Cl₂/(2M NH₃ in MeOH)=92/8] to afford a mixture of the title compounds. MS (ESI+) m/z 437.2 (M+H).

Example 7-D: (±)-2-(Amino(2-methoxy-4,6-dimethylphenyl)methyl)-1H-benzo[d]imidazole-5-carbonitrile

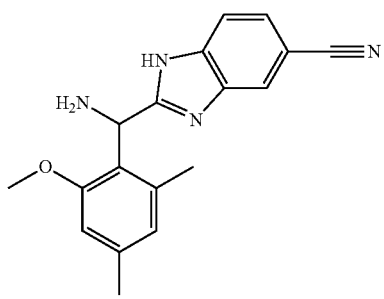 [SMILES: COc1cc(C)cc(C)c1C(N)c1nc2cc(C#N)ccc2[nH]1]

The title compound was synthesized from a mixture of (±)-2-(amino(2-methoxy-4,6-dimethylphenyl)methyl)-1-((2-(trimethylsilyl)ethoxy)methyl)-1H-benzo[d]imidazole-5-carbonitrile and (±)-2-(amino(2-methoxy-4,6-dimethylphenyl)methyl)-1-((2-(trimethylsilyl)ethoxy)methyl)-1H-benzo[d]imidazole-6-carbonitrile analogously to Example 1-C. ¹H NMR (with ~5 uM TFA, 400 MHz, CD₃CN) δ 7.90 (s, 1H), 7.59 (d, J=8.60 Hz, 1H), 7.49 (dd, J=1.50, 8.60 Hz, 1H), 6.73 (s, 1H), 6.69 (s, 1H), 5.75 (s, 1H), 3.55 (s, 3H), 2.37 (s, 3H), 2.30 (s, 3H). HRMS; calcd. for C₁₉H₂₀N₃O₂ 307.1553 (M+H). found 307.1551.

Example 8

Example 8-A: (±)-N-(1-(5-Cyano-1-((2-(trimethylsilyl)ethoxy)methyl)-1H-benzo[d]imidazol-2-yl)-1-(2-methoxy-4,6-dimethylphenyl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(2-methoxy-4,6-dimethylphenyl)ethyl)-2-methylpropane-2-sulfinamide

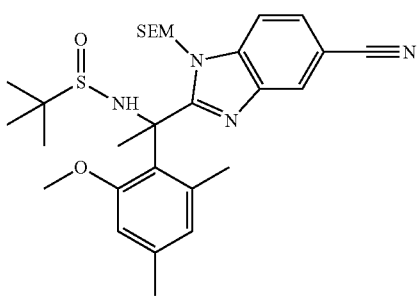

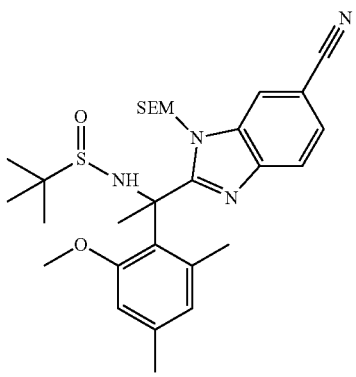

To a solution of a mixture of (±)-N-((5-cyano-1-((2-(trimethylsilyl)ethoxy)methyl)-1H-benzo[d]imidazol-2-yl)(2-methoxy-4,6-dimethylphenyl(methylene)-2-methylpropane-2-sulfinamide and (±)-N-((6-cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide (Example 7-A) (1.078 g, 2 mmol) in THF (10 ml) at 0° C. was added MeMgI in Et₂O (2 ml, 6 mmol) over 10 min. The mixture was then stirred at 0° C. for 1 h, and then quenched with half satd. aq. KHSO₄. The mixture was then diluted with EtOAc. The mixture was filtered through a plug of Celite®, which was rinsed with EtOAc. The bi-layer was partitioned. The organic phase was washed successively with H₂O and brine, dried over Na₂SO₄, filtered, and then concentrated to furnish a mixture of the title compounds. MS (ESI+) m/z 553.2 (M−H).

Example 8-B: (±)-2-(1-Amino-1-(2-methoxy-4,6-dimethylphenyl)ethyl)-1H-benzo[d]imidazole-5-carbonitrile

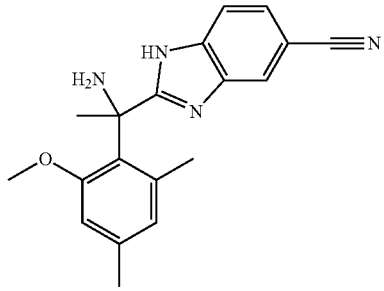 [SMILES: COc1cc(C)cc(C)c1C(C)(N)c1nc2cc(C#N)ccc2[nH]1]

A solution of a mixture of (±)-N-(1-(5-cyano-1-((2-(trimethylsilyl)ethoxy)methyl)-1H-benzo[d]imidazol-2-yl)-1-(2-methoxy-4,6-dimethylphenyl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(2-methoxy-4,6-dimethylphenyl)ethyl)-2-methylpropane-2-sulfinamide (1.110 g, 2 mmol) in 1M HCl in MeOH (20 mL) was stirred at room temperature for 3 h, and then quenched with 5% NaHCO$_3$, and then diluted with EtOAc. The mixture was filtered through a plug of celite, which was rinsed with EtOAc. The organic layer was washed successively with H$_2$O and brine, dried over Na$_2$SO$_4$, filtered, and then concentrated. The resulting residue was purified by silica gel flash column chromatography (28% aq. NH$_4$OH in CH$_2$Cl$_2$/MeOH=99/1 to 92/8), followed by RP-HPLC (HC-A) to afford the title compounds. $^1$H NMR (400 MHz, CD$_3$CN) δ 7.99 (br. s., 1H), 7.64 (d, J=8.34 Hz, 1H), 7.53 (dd, J=1.50, 8.30 Hz, 1H), 6.75 (s, 1H), 6.59 (s, 1H), 3.65 (s, 3H), 2.25 (s, 3H), 2.12 (s, 3H), 1.80 (s, 3H). HRMS; calcd. for C$_{19}$H$_{21}$N$_4$O 321.1710 (M+H). found 321.1715.

Example 9

Example 9-A: (±)-N-((5-Cyano-1-((2-(trimethylsilyl)ethoxy)methyl)-1H-benzo[d]imidazol-2-yl)(cyclopropyl)(2-methoxy-4,6-dimethylphenyl)methyl)-2-methylpropane-2-sulfinamide and (±)-N-((6-cyano-1-((2-(trimethylsilyl)ethoxy)methyl)-1H-benzo[d]imidazol-2-yl)(cyclopropyl)(2-methoxy-4,6-dimethylphenyl)methyl)-2-methylpropane-2-sulfinamide

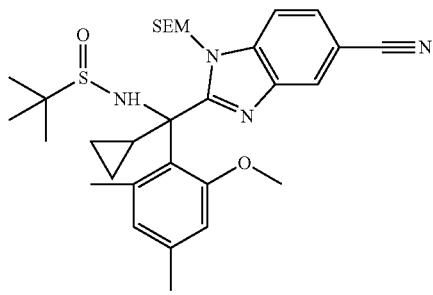

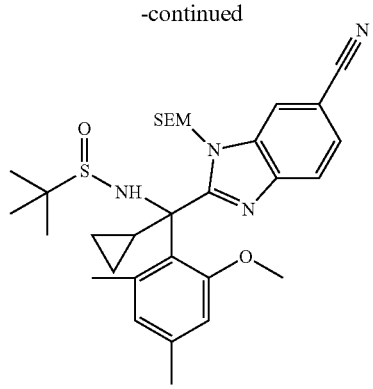

The title compound was synthesized from a mixture of (±)-N-((5-cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide and (±)-N-((6-cyano-1-((2-(trimethylsilyl)ethoxy)methyl)-1H-benzo[d]imidazol-2-yl)(2-methoxy-4,6-dimethylphenyl)methylene)-2-methylpropane-2-sulfinamide (Example 7-A) analogously to Example 8-A by using cyclopropylmagnesium bromide in the place of methylmagnesium iodide. MS (ESI+) m/z 581.3 (M+H).

Example 9-B: (±)-N-((6-cyano-1H-benzo[d]imidazol-2-yl)(cyclopropyl)(2-methoxy-4,6-dimethylphenyl)methyl)-2-methylpropane-2-sulfinamide

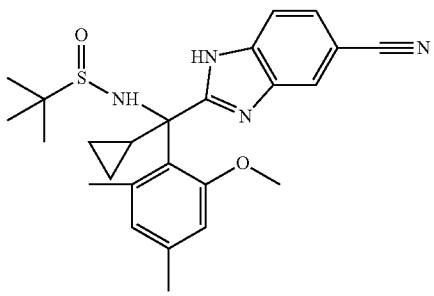 [SMILES: COc1cc(C)cc(C)c1C(NS(=O)C(C)(C)C)(c1nc2cc(C#N)ccc2[nH]1)C1CC1]

The title compound was synthesized from a mixture of (±)-N-((5-cyano-1-((2-(trimethylsilyl)ethoxy)methyl)-1H-benzo[d]imidazol-2-yl)(cyclopropyl)(2-methoxy-4,6-dimethylphenyl)methyl)-2-methylpropane-2-sulfinamide and (±)-N-((6-cyano-1-((2-(trimethylsilyl)ethoxy)methyl)-1H-benzo[d]imidazol-2-yl)(cyclopropyl)(2-methoxy-4,6-dimethylphenyl)methyl)-2-methylpropane-2-sulfinamide analogously to Example 2-C. MS (ESI+) m/z 451.1 (M+H).

Example 9-C: (±)-2-(Amino(cyclopropyl)(2-methoxy-4,6-dimethylphenyl)methyl)-1H-benzo[d]imidazole-5-carbonitrile

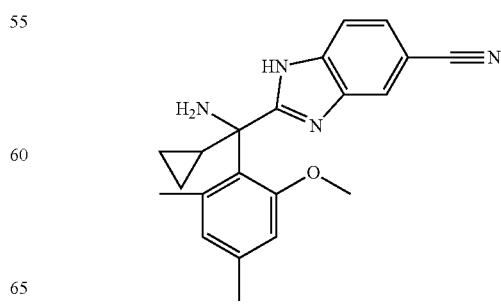

The title compound was synthesized from (±)-N-((6-cyano-1H-benzo[d]imidazol-2-yl)(cyclopropyl)(2-methoxy-4,6-dimethylphenyl)methyl)-2-methylpropane-2-sulfinamide analogously to Example 1-C. $^1$H NMR (with ~5 μL TFA, 400 MHz, CD$_3$CN) δ 8.01 (br. s., 1H), 7.62 (br. s., 1H), 7.54 (dd, J=1.50, 8.30 Hz, 1H), 6.74 (s, 1H), 6.62 (s, 1H), 3.66 (s, 3H), 2.28-2.38 (m, 1H), 2.26 (s, 3H), 1.78 (br. s, 3H), 0.79-0.90 (m, 1H), 0.65-0.80 (m, 1H), 0.39-0.57 (m, 1H), 0.18-0.37 (m, 1H). HRMS; calcd. for C$_{21}$H$_{23}$N$_4$O 347.1872 (M+H). found 347.1871.

Example 10

Example 10-A: (±)-Methyl 2-(1-(5-cyano-1-((2-(trimethylsilyl)ethoxy)methyl)-1H-benzo[d]imidazol-2-yl)-2,2,2-trifluoro-1-(2-methoxy-4,6-dimethylphenyl)ethoxy)acetate and (±)-methyl 2-(1-(6-cyano-1-((2-(trimethylsilyl)ethoxy)methyl)-1H-benzo[d]imidazol-2-yl)-2,2,2-trifluoro-1-(2-methoxy-4,6-di methyl phenyl)ethoxy)acetate

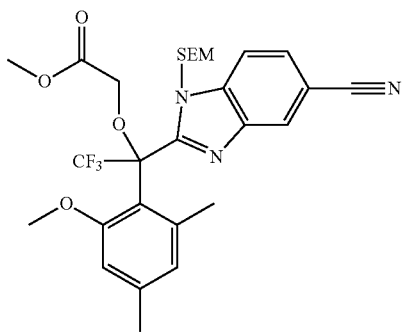

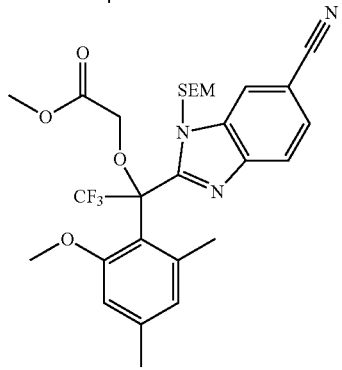

To a solution of a mixture of (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-5-carbonitrile and (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-6-carbonitrile (Example 3-A) (154 mg, 0.305 mmol) and methyl bromoacetate (0.056 ml, 0.609 mmol) in THF (4 ml) at 0° C. was added NaH (60% in oil, 24.4 mg, 0.61 mmol). The mixture was then stirred at the same temperature for 1.5 h, and then quenched with AcOH. The mixture was then stirred at room temperature for 0.25 h, and then diluted with Et$_2$O. The organic phase was washed successively with 5% aq. NaHCO$_3$ (twice), H$_2$O, and brine, dried over Na$_2$SO$_4$, filtered, and then concentrated. The resulting residue was purified by silica gel flash column chromatography [isocratic, heptane/(30% EtOAc in CH$_2$Cl$_2$)=66/34] to afford a mixture of the title compounds. MS (ESI+) m/z 577.7 (M+H).

Example 10-B: (±)-Methyl 2-(1-(5-cyano-1H-benzo[d]imidazol-2-yl)-2,2,2-trifluoro-1-(2-methoxy-4,6-dimethylphenyl)ethoxy)acetate

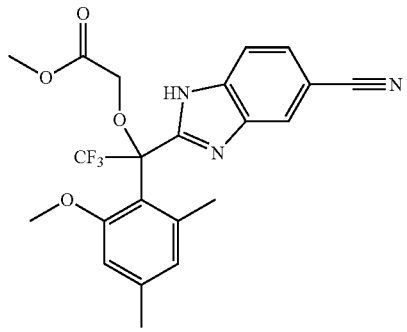 [SMILES: COC(=O)COC(c1nc2cc(C#N)ccc2[nH]1)(c1c(C)cc(C)cc1OC)C(F)(F)F]

The title compound was synthesized from a mixture of (±)-methyl 2-(1-(5-cyano-1-((2-(trimethylsilyl)ethoxy)methyl)-1H-benzo[d]imidazol-2-yl)-2,2,2-trifluoro-1-(2-methoxy-4,6-dimethylphenyl)ethoxy)acetate and (±)-methyl 2-(1-(6-cyano-1-((2-(trimethylsilyl)ethoxy)methyl)-1H-benzo[d]imidazol-2-yl)-2,2,2-trifluoro-1-(2-methoxy-4,6-dimethylphenyl)ethoxy)acetate analogously to Example 1-C. MS (ESI+) m/z 448.1 (M+H).

Example 10-C: (±)-2-(1-(5-Cyano-1H-benzo[d]imidazol-2-yl)-2,2,2-trifluoro-1-(2-methoxy-4,6-dimethylphenyl)ethoxy)acetamide

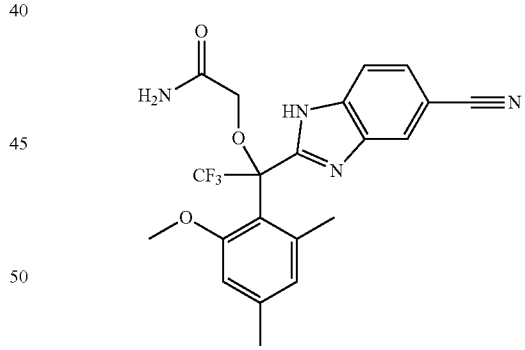

A solution of (±)-methyl 2-(1-(5-cyano-1H-benzo[d]imidazol-2-yl)-2,2,2-trifluoro-1-(2-methoxy-4,6-dimethylphenyl)ethoxy)acetate (60 mg, 0.103 mmol) in 7N NH$_3$ in MeOH (10 ml) was stirred at 60° C. for 1.25 h, and then concentrated. The resulting residue was triturated with CH$_3$CN. The resulting solid was collected by filtration, and then dried up to afford the title compound. $^1$H NMR (+~5 μL TFA, 400 MHz, CD$_3$CN) δ 8.08 (d, J=0.76 Hz, 1H), 7.72 (d, J=8.60 Hz, 1H), 7.64 (dd, J=1.50, 8.60 Hz, 1H), 6.79 (s, 1H), 6.69 (s, 1H), 6.48 (br. s., 1H), 5.99 (br. s., 1H), 4.02 (d, J=14.80 Hz, 1H), 3.76 (d, J=14.80 Hz, 1H), 3.18 (s, 3H), 2.45 (s, 3H), 2.29 (s, 3H). HRMS; calcd. for C$_{21}$H$_{20}$F$_3$N$_4$O$_3$ 433.1488 (M+H). found 433.1476.

Example 11

Example 11-A: (±)-2-(2,2,2-Trifluoro-1-methoxy-1-(2-methoxy-4,6-dimethylphenyl)ethyl)-1-((2-(trimethylsilyl)ethoxy)methyl)-1H-benzo[d]imidazole-5-carbonitrile and (±)-2-(2,2,2-trifluoro-1-methoxy-1-(2-methoxy-4,6-dimethylphenyl)ethyl)-1-((2-(trimethylsilyl)ethoxy)methyl)-1H-benzo[d]imidazole-6-carbonitrile

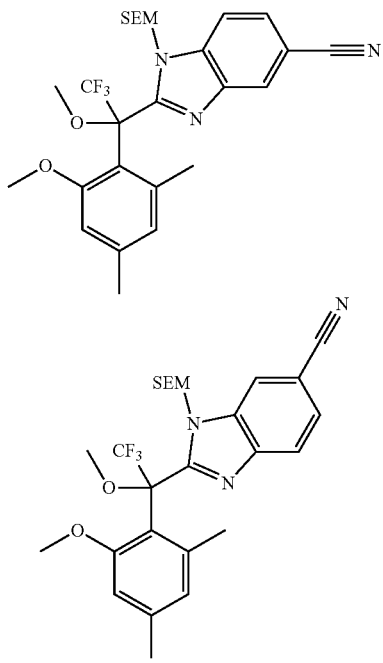

To a solution of a mixture of (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-5-carbonitrile and (±)-2-(2,2,2-trifluoro-1-hydroxy-1-(2-methoxy-4,6-dimethylphenyl)ethyl)-1-((2-(trimethylsilyl)ethoxy)methyl)-1H-benzo[d]imidazole-6-carbonitrile (Example 3-A) (0.464 g, 0.918 mmol) and MeI (0.12 mL, 1.919 mmol) in DMF (10 ml) at 0° C. was added NaH (0.08 g, 2.000 mmol). The mixture was then stirred at the same temperature for 2 h, and then quenched with MeOH, followed by half satd. KHSO$_4$. The mixture was extracted with EtOAc. The organic phase was washed successively with H$_2$O and brine, dried over Na$_2$SO$_4$, filtered, and then concentrated to furnish a mixture of the title compounds. MS (ESI+) m/z 520.4 (M+H).

Example 11-B: a) (±)-2-(2,2,2-Trifluoro-1-methoxy-1-(2-methoxy-4,6-dimethylphenyl)ethyl)-1H-benzo[d]imidazole-5-carbonitrile

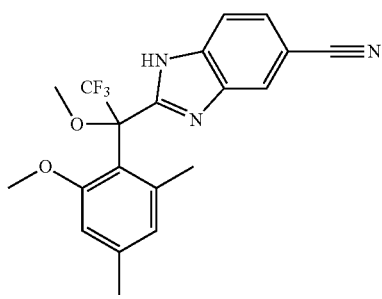 [SMILES: COc1cc(C)cc(C)c1C(OC)(c1nc2cc(C#N)ccc2[nH]1)C(F)(F)F]

The title compound was synthesized from a mixture of (±)-2-(2,2,2-trifluoro-1-methoxy-1-(2-methoxy-4,6-dimethylphenyl)ethyl)-1-((2-(trimethylsilyl)ethoxy)methyl)-1H-benzo[d]imidazole-5-carbonitrile and (±)-2-(2,2,2-trifluoro-1-methoxy-1-(2-methoxy-4,6-dimethylphenyl)ethyl)-1-((2-(trimethylsilyl)ethoxy)methyl)-1H-benzo[d]imidazole-6-carbonitrile analogously to Example 2-C. $^1$H NMR (with ~5 μL TFA, 400 MHz, CD$_3$CN) δ 8.03 (s, 1H), 7.67 (d, J=8.30 Hz, 1H), 7.58 (dd, J=1.50, 8.30 Hz, 1H), 6.76 (s, 1H), 6.67 (s, 1H), 3.17 (d, J=1.01 Hz, 3H), 3.14 (s, 3H), 2.45 (s, 3H), 2.28 (s, 3H). HRMS; calcd. for C$_{20}$H$_{19}$F$_3$N$_3$O$_2$ 390.1429 (M+H). found 390.1414. b) (+) or (−)-2-(2,2,2-trifluoro-1-methoxy-1-(2-methoxy-4,6-dimethylphenyl)ethyl)-1H-benzo[d]imidazole-5-carbonitrile and (−) or (+)-2-(2,2,2-trifluoro-1-methoxy-1-(2-methoxy-4,6-dimethylphenyl)ethyl)-1H-benzo[d]imidazole-5-carbonitrile Resolution of the enantiomers (±)-2-(2,2,2-trifluoro-1-methoxy-1-(2-methoxy-4,6-dimethylphenyl)ethyl)-1H-benzo[d]imidazole-5-carbonitrile was achieved by chiral SFC using a AD-H column with 10% EtOH in CO$_2$ to give (+) or (−)-2-(2,2,2-trifluoro-1-methoxy-1-(2-methoxy-4,6-dimethylphenyl)ethyl)-1H-benzo[d]imidazole-5-carbonitrile (t$_r$=1.9 min) and (−) or (+)-2-(2,2,2-trifluoro-1-methoxy-1-(2-methoxy-4,6-dimethylphenyl)ethyl)-1H-benzo[d]imidazole-5-carbonitrile (t$_r$=2.5 min).

Example 12

Example 12-A: (±)-2-((2,6-Dimethoxy-4-methylphenyl)(hydroxy)methyl)-1-((2-(trimethylsilyl)ethoxy)methyl)-1H-benzo[d]imidazole-5-carbonitrile and (±)-2-((2,6-dimethoxy-4-methylphenyl)(hydroxy)methyl)-1-((2-(trimethylsilyl)ethoxy)methyl)-1H-benzo[d]imidazole-6-carbonitrile

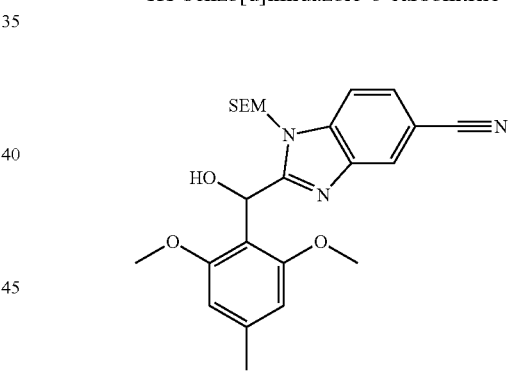

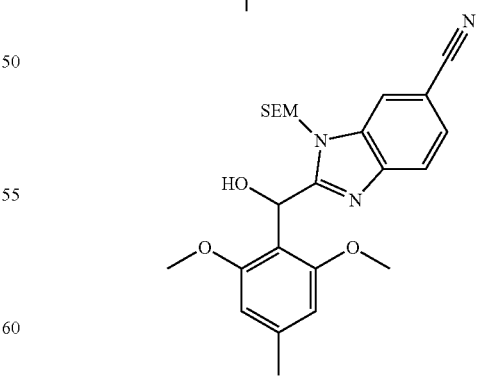

The mixture of title compounds was synthesized from a mixture of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (Example 1-A) and 2,6-dimethoxy-4-methylbenzaldehyde (CAS#6937-96-8) analogously to Example 1-B. MS (ESI+) m/z 454.1 (M+H).

Example 12-B: 2-(2,6-Dimethoxy-4-methylbenzoyl)-1-((2-(trimethylsilyl)ethoxy)methyl)-1H-benzo[d]imidazole-5-carbonitrile and 2-(2,6-dimethoxy-4-methylbenzoyl)-1-((2-(trimethylsilyl)ethoxy)methyl)-1H-benzo[d]imidazole-6-carbonitrile

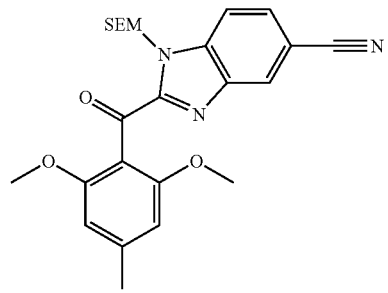

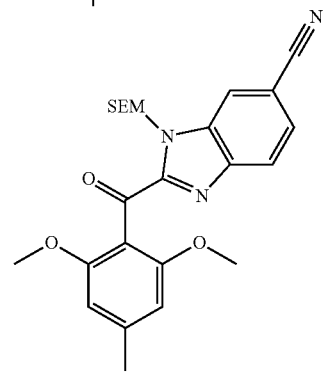

The mixture of title compounds was synthesized from a mixture of (±)-2-((2,6-dimethoxy-4-methylphenyl)(hydroxy)methyl)-1-((2-(trimethylsilyl)ethoxy)methyl)-1H-benzo[d]imidazole-5-carbonitrile and (±)-2-((2,6-dimethoxy-4-methylphenyl)(hydroxy)methyl)-1-((2-(trimethylsilyl)ethoxy)methyl)-1H-benzo[d]imidazole-6-carbonitrile analogously to Example 2-A. MS (ESI+) m/z 452.1 (M+H).

Example 12-C: 2-((2,6-dimethoxy-4-methylphenyl)(hydroxy)methyl)-1H-benzo[d]imidazole-5-carbonitrile (A) and 2-(1-(2,6-dimethoxy-4-methylphenyl)-2,2,2-trifluoro-1-hydroxyethyl)-1H-benzo[d]imidazole-5-carbonitrile (B)

Example 12-C (A)

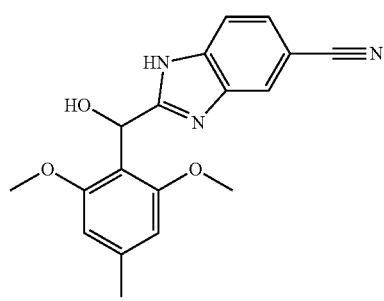

Example 12-C (B)

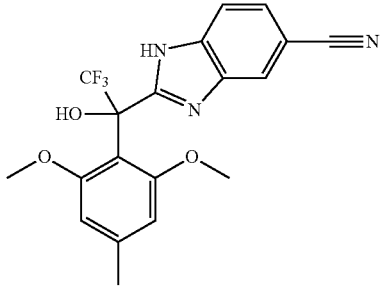

To a solution of 2-(2,6-dimethoxy-4-methylbenzoyl)-1-((2-(trimethylsilyl)ethoxy)methyl)-1H-benzo[d]imidazole-6-carbonitrile (0.993 g, 2.2 mmol) and trimethyl(trifluoromethyl)silane (0.688 ml, 4.40 mmol) in THF (10 ml) at room temperature was added dropwise TBAF in THF (1M, 6.60 ml, 6.60 mmol), and then the mixture was then stirred at room temperature for 3 h. The reaction did not complete, and the starting material was observed in LCMS. The reaction was quenched with MeOH. The mixture was stirred at room temperature for 16 h, and then diluted with Et$_2$O. The mixture was washed successively with 5% aq. NaHCO$_3$, half satd. aq. KHSO$_4$, H$_2$O and brine, dried over Na$_2$SO$_4$, filtered, and concentrated. The resulting residue and 1M HCl in MeOH (20 ml) was stirred at 60° C. for 14 h, and then diluted with CH$_2$Cl$_2$. The mixture was successively washed by 5% aq. NaHCO$_3$, H$_2$O and brine, dried over Na$_2$SO$_4$, filtered, and then concentrated. The resulting residue was purified by silica gel flash column chromatography (CH$_2$Cl$_2$/EtOAc=97/3 to 84/16). The obtained mixture was dissolved in MeOH (10 mL) was added NaBH$_4$ (135 mg, 3.58 mmol). The mixture was then stirred at room temperature for 2 h, and then diluted with CH$_2$Cl$_2$. The mixture was washed successively with 5% aq. NaHCO$_3$, H$_2$O and brine, dried over Na$_2$SO$_4$, filtered, and then concentrated to furnish a mixture of the title compounds. MS for Example 12-C(A) (ESI+) m/z 324.1 (M+H). MS for Example 12-C(B) (ESI+) m/z 392.0 (M+H).

Example 12-D: (±)-2-((2,6-Dimethoxy-4-methylphenyl)(methylamino)methyl)-1H-benzo[d]imidazole-5-carbonitrile (A) and (±)-2-(1-(2,6-dimethoxy-4-methylphenyl)-2,2,2-trifluoro-1-(methylamino)ethyl)-1H-benzo[d]imidazole-5-carbonitrile (B)

Example 12-D (A)

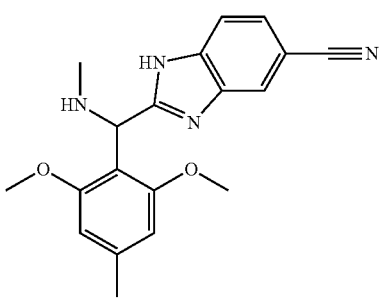

Example 12-D (B)

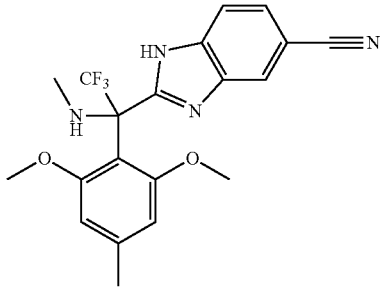

The title compounds were synthesized and isolated from a mixture of (±)-2-((2,6-dimethoxy-4-methylphenyl)(hydroxy)methyl)-1H-benzo[d]imidazole-5-carbonitrile and (±)-2-(1-(2, 6-dimethoxy-4-methylphenyl)-2,2,2-trifluoro-1-hydroxyethyl)-1H-benzo[d]imidazole-5-carbonitrile analogously to Example 5.

Analytical data for Example 12-D (A): $^1$H NMR (with ~5 μL TFA, 400 MHz, CD$_3$CN) δ 7.88 (d, J=0.76 Hz, 1H), 7.58 (d, J=8.30 Hz, 1H), 7.47 (dd, J=1.52, 8.34 Hz, 1H), 6.51 (s, 2H), 5.67 (s, 1H), 3.68 (s, 6H), 2.46 (s, 3H), 2.33 (s, 3H). HRMS; calcd. for $C_{19}H_{21}N_4O_2$ 337.1665 (M+H). found 337.1666.

Analytical data for Example 12-D (B): (with ~5 uM TFA, 400 MHz, CD$_3$CN) δ 8.06 (br. s, 1H), 7.67 (br. d, J=8.30 Hz, 1H), 7.59 (dd, J=1.50, 8.30 Hz, 1H), 6.56 (s, 2H), 3.47 (s, 6H), 2.34 (s, 3H), 2.32 (s, 3H). HRMS; calcd. for $C_{20}H_{20}F_3N_4O_2$ 405.1538 (M+H). found 405.1535.

Compounds of invention are active on factor B inhibition. Data on Table 1 collected using the assay of Biological Example 1.

TABLE 1

| Example number | IC$_{50}$ (μM) |
| --- | --- |
| 1-C | 5.75 |
| 2-C | 1.45 |
| 3-B | 0.39 |
| 5 b) (t$_r$ = 3.7 min) | 0.023 |
| 5 b) (t$_r$ = 4.7 min) | 1.9 |
| 6-A | 0.38 |
| 6-B | 1.98 |
| 6-C | 3.13 |
| 6-D | 1.57 |
| 7-D | 8.7 |
| 8-B | 6.9 |
| 9-C | 1.5 |
| 12-D (A) | 13.9 |
| 12-D (B) | 11.1 |

Compounds of invention are active on factor B inhibition. Data on Table 2 collected using the assay of Biological Example 2.7.

TABLE 2

| Example number | IC$_{50}$ (μM) |
| --- | --- |
| 4 | 98.9 |
| 6-E | 7 |
| 10-C | 0.47 |
| 11-B b) (t$_r$ = 1.9 min) | 41.1 |
| 11-B b) (t$_r$ = 2.5 min) | 0.055 |

What is claimed is:

1. A compound, or salt or tautomer thereof, according to Formula (I):

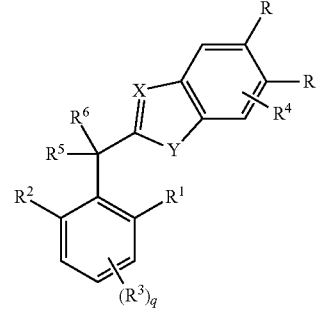

Wherein

X is N or CH;

Y is N(H) or O;

one occurrence of R is cyano and the other occurrence of R is hydrogen or $R^4$;

$R^1$ is hydrogen, halogen, hydroxyl, $C_1$-$C_6$alkyl, $C_2$-$C_6$alkenyl, $C_3$-$C_6$cycloalkyl, $C_1$-$C_6$alkoxy, haloC$_1$-C$_6$alkyl, haloC$_1$-C$_6$alkoxy, or S(O)$_p$C$_1$-C$_6$alkyl;

$R^2$ is halogen, hydroxyl, $C_1$-$C_6$alkyl, $C_2$-$C_6$alkenyl, $C_3$-$C_6$cycloalkyl, $C_1$-$C_6$alkoxy, haloC$_1$-C$_6$alkyl, or S(O)$_p$C$_1$-C$_6$alkyl;

p is 0, 1, or 2;

q is 0, 1, or 2;

$R^3$ is hydrogen, halogen, cyano, $C_1$-$C_4$alkyl, haloC$_1$-C$_4$alkyl C$_1$-C$_4$alkoxy, or haloC$_1$-C$_4$alkoxy;

$R^4$ is 0, 1, or 2 substituents independently selected at each occurrence from halogen and $C_1$-$C_6$alkyl;

$R^5$ is hydrogen, $C_1$-$C_6$alkyl, haloC$_1$-C$_6$alkyl, or $C_3$-$C_6$cycloalkyl;

$R^6$ is hydroxy, amino, $C_1$-$C_6$alkyl, $C_1$-$C_6$alkoxy, $C_1$-$C_4$haloalkoxy, $C_1$-$C_6$alkoxyC$_1$-C$_6$alkyl, mono- and di-C$_1$-C$_4$alkylamino, amino C$_1$-C$_6$alkylamino, [CR$^8_2$]$_n$R$^7$, [CR$^8_2$]$_n$C(O)R$^7$, O[CR$^8_2$]$_n$R$^7$, NHC(O)C$_1$-C$_6$alkyl, NHS(O$_2$)C$_1$-C$_6$alkyl, (CH$_2$)$_n$R$^9$, O(CH$_2$)$_n$R$^9$, C(O)R$^7$, N(H)[CR$^4_2$]$_n$R$^7$, O[CR$^4_2$]$_n$C(O)R$^7$, N(H)[CR$^8_2$]$_n$C(O)R$^7$ or tetrazolyl;

n is 1, 2, 3 or 4;

$R^7$ is hydroxy, $C_1$-$C_4$alkoxy, amino or mono- and di-C$_1$-C$_4$alkylamino;

$R^8$ is independently selected at each occurrence from hydrogen, halogen or $C_1$-$C_4$alkyl;

$R^9$ is a 5 member heteroaryl having 1 to 4 ring heteroatoms selected from N, O or S and optionally substituted with 0, 1, or 2 $C_1$-$C_4$alkyl groups.

2. The compound of claim 1, wherein X is N and Y is N(H) or O.

3. The compound of claim 1 wherein X is N and Y is N(H).

4. The compound of claim 1, wherein $R^4$ is absent.

5. The compound of claim 1, wherein $R^1$ is hydrogen, $C_1$-$C_4$alkyl or $C_1$-$C_4$alkoxy.

6. The compound of claim 1, wherein $R^2$ is $C_1$-$C_4$alkyl or $C_1$-$C_4$alkoxy.

7. The compound of claim 1, or salt or tautomer thereof, according to Formula (II):

(II)

[Structure: benzimidazole connected via CR⁵R⁶ to a phenyl ring with substituents R¹, R², R³, R¹⁰; benzimidazole bears two R groups]

Wherein one occurrence of R is cyano and the other occurrence of R is hydrogen;
R¹ is hydrogen, methyl, methoxy, ethyl or ethyoxy;
R² is methyl, methoxy, ethyl or ethyoxy;
R³ is hydrogen, methyl, methoxy, ethyl or ethyoxy; and
R¹⁰ is hydrogen or halogen.

8. The compound of claim 1, wherein R⁵ is hydrogen, $C_1$-$C_4$alkyl, halo $C_1$-$C_4$alkyl, or $C_3$-$C_6$cycloalkyl.

9. The compound of claim 1, wherein R⁶ is hydroxyl, amino, $C_1$-$C_4$alkyl, methoxy, trifluoromethoxy, mono- and di-$C_1$-$C_4$alkyl amino, or $CH_2C(O)NH_2$.

10. The compound of claim 7, wherein
One occurrence of R is cyano and the other occurrence of R is hydrogen;
R¹ is hydrogen, methyl, methoxy, ethyl or ethyoxy;
R² is methyl, methoxy, ethyl or ethyoxy;
R³ is hydrogen or methyl;
R⁵ is hydrogen, methyl, cyclopropyl or trifluoromethyl;
R⁶ is hydroxyl, amino, methoxy, trifluoromethoxy, methylamino or $CH_2C(O)NH_2$; and
R¹⁰ is hydrogen, chloro or bromo.

11. The compound of claim 1, or a salt, stereoisomer or tautomer thereof, which compound is selected from the group consisting of (±)-2-(Hydroxy(2-methoxy-4,6-dimethylphenyl)methyl)-1H-benzo[d]imidazole-5-carbonitrile;
(±)-2-(1-Hydroxy-1-(2-methoxy-4,6-dimethylphenylethyl)-1H-benzo[d]imidazole-5-carbonitrile;
(±)-2-(2,2,2-Trifluoro-1-hydroxy-1-(2-methoxy-4,6-dimethylphenyhethyl)-1H-benzo[d]imidazole-5-carbonitrile;
(±)-2-(1-(3-bromo-6-methoxy-2,4-dimethylphenyl)-2,2,2-trifluoro-1-hydroxyethyl)-1H-benzo[d]imidazole-5-carbonitrile;
(+) or (−)-2-(2,2,2-Trifluoro-1-(2-methoxy-4,6-dimethylphenyl)-1-(methylamino)ethyl)-1H-benzo[d]imidazole-5-carbonitrile;
(−) or (+)-2-(2,2,2-Trifluoro-1-(2-methoxy-4,6-dimethylphenyl)-1-(methylamino)ethyl)-1H-benzo[d]imidazole-5-carbonitrile;
(±)-2-(2,2,2-Trifluoro-1-(2-methoxy-4-methylphenyl)-1-(methylamino)ethyl)-1H-benzo[d]imidazole-5-carbonitrile;
(±)-2-(1-(3-Chloro-6-methoxy-2,4-dimethylphenyl)-2,2,2-trifluoro-1-(methylamino)ethyl)-1H-benzo[d]imidazole-5-carbonitrile;
(±)-2-(2,2,2-Trifluoro-1-(2-methoxy-6-methylphenyl)-1-(methylamino)ethyl)-1H-benzo[d]imidazole-5-carbonitrile;
(±)-2-(1-Amino-2,2,2-trifluoro-1-(2-methoxy-4,6-dimethylphenyl)ethyl)-1H-benzo[d]imidazole-5-carbonitrile;
(±)-2-(1-(3-Bromo-6-methoxy-2,4-dimethylphenyl)-2,2,2-trifluoro-1-(methylamino)ethyl)-1H-benzo[d]imidazole-5-carbonitrile;
(±)-2-(Amino(2-methoxy-4,6-dimethylphenyl)methyl)-1H-benzo[d]imidazole-5-carbonitrile;
(±)-2-(1-Amino-1-(2-methoxy-4,6-dimethylphenyl)ethyl)-1H-benzo[d]imidazole-5-carbonitrile;
(±)-2-(Amino(cyclopropyl)(2-methoxy-4,6-dimethylphenyl)methyl)-1H-benzo[d]imidazole-5-carbonitrile;
(±)-2-(1-(5-Cyano-1H-benzo[d]imidazol-2-yl)-2,2,2-trifluoro-1-(2-methoxy-4,6-dimethylphenyl)ethoxy)acetamide;
(+) or (−)-2-(2,2,2-trifluoro-1-methoxy-1-(2-methoxy-4,6-dimethylphenyl)ethyl)-1H-benzo[d]imidazole-5-carbonitrile;
(−) or (+)-2-(2,2,2-trifluoro-1-methoxy-1-(2-methoxy-4,6-dimethylphenyl)ethyl)-1H-benzo[d]imidazole-5-carbonitrile; and
(±)-2((2,6-Dimethoxy-4-methylphenyl)(methylamino)methyl)-1H-benzo[d]imidazole-5-carbonitrile; (±)-2-(1-(2,6-dimethoxy-4-methylphenyl)-2,2,2-trifluoro-1-(methylamino)ethyl)-1H-benzo[d]imidazole-5-carbonitrile.

12. A pharmaceutical composition comprising one or more pharmaceutically acceptable carriers and a therapeutically effective amount of a compound of claim 1.

* * * * *